(12) United States Patent
Hamilton et al.

(10) Patent No.: US 6,218,424 B1
(45) Date of Patent: Apr. 17, 2001

(54) HETEROCYCLIC KETONE AND THIOESTER COMPOUNDS AND USES

(75) Inventors: Gregory S. Hamilton, Catonsville; Jia-He Li, Cockeysville, both of MD (US)

(73) Assignee: GPI NIL Holdings, Inc., Wilmington, DE (US)

( * ) Notice: Subject to any disclaimer, the term of this patent is extended or adjusted under 35 U.S.C. 154(b) by 0 days.

(21) Appl. No.: 09/444,200

(22) Filed: Nov. 22, 1999

Related U.S. Application Data

(63) Continuation-in-part of application No. 08/904,461, filed on Aug. 1, 1997, now Pat. No. 5,990,131, which is a continuation-in-part of application No. 08/721,765, filed on Sep. 25, 1996, now Pat. No. 5,786,378.

(51) Int. Cl.$^7$ .......................... A61K 31/40; C07D 207/04
(52) U.S. Cl. .......................... 514/423; 548/530; 548/539; 548/540; 546/226; 546/279.1; 514/315; 514/330; 514/343
(58) Field of Search .................................. 514/330, 423, 514/343, 315; 546/226, 279.1; 548/540, 539, 530; 435/240.2

(56) References Cited

U.S. PATENT DOCUMENTS

| | | |
|---|---|---|
| 3,203,961 | 8/1965 | Wu . |
| 3,458,515 | 7/1969 | Archibald et al. . |
| 3,459,770 | 8/1969 | Freed et al. . |

(List continued on next page.)

FOREIGN PATENT DOCUMENTS

| | | |
|---|---|---|
| 3508251 | 9/1986 | (DE) . |
| 3931051 | 3/1990 | (DE) . |
| 4015255 | 11/1991 | (DE) . |
| 12401 | 6/1980 | (EP) . |
| 48159 | 3/1982 | (EP) . |
| 50800 | 5/1982 | (EP) . |
| 73143 | 3/1983 | (EP) . |
| 88350 | 9/1983 | (EP) . |
| 196841 | 10/1986 | (EP) . |
| 260118 | 3/1988 | (EP) . |
| 333174 | 9/1989 | (EP) . |
| 352000 | 1/1990 | (EP) . |
| 378318 | 7/1990 | (EP) . |
| 405994 | 1/1991 | (EP) . |
| 419049 | 3/1991 | (EP) . |
| 468339 | 1/1992 | (EP) . |
| 572365 | 12/1993 | (EP) . |
| 0 597 291 | 5/1994 | (EP) . |
| 652229 | 5/1995 | (EP) . |
| 2247456 | 3/1992 | (GB) . |
| 04149166 | 5/1992 | (JP) . |
| 05178824 | 7/1993 | (JP) . |
| WO95/35308 | 12/1985 | (WO) . |
| WO8809789 | 12/1988 | (WO) . |
| WO9012805 | 11/1990 | (WO) . |
| WO91/04985 | 4/1991 | (WO) . |
| WO9113088 | 9/1991 | (WO) . |
| WO92/00278 | 1/1992 | (WO) . |
| WO92/04370 | 3/1992 | (WO) . |
| WO9203472 | 3/1992 | (WO) . |
| WO92/16501 | 10/1992 | (WO) . |
| WO92/18478 | 10/1992 | (WO) . |
| WO92/19593 | 11/1992 | (WO) . |
| WO92/19745 | 11/1992 | (WO) . |
| WO92/21313 | 12/1992 | (WO) . |
| WO93/07269 | 4/1993 | (WO) . |
| WO93/13066 | 7/1993 | (WO) . |
| WO93/23548 | 11/1993 | (WO) . |
| WO93/25546 | 12/1993 | (WO) . |
| WO94/05639 | 3/1994 | (WO) . |
| WO94/07858 | 4/1994 | (WO) . |
| WO94/13629 | 6/1994 | (WO) . |
| WO95/12572 | 5/1995 | (WO) . |
| WO95/24385 | 9/1995 | (WO) . |
| WO95/26337 | 10/1995 | (WO) . |
| WO95/35367 | 12/1995 | (WO) . |
| WO96/06097 | 2/1996 | (WO) . |
| WO96/15101 | 5/1996 | (WO) . |
| WO9617816 | 6/1996 | (WO) . |
| WO96/41609 | 12/1996 | (WO) . |
| WO97/36869 | 10/1997 | (WO) . |
| 9207782 | 4/1992 | (ZA) . |

OTHER PUBLICATIONS

Holt, D.A. et al.: Structure–activity studies of synthetic FKBP ligands as peptidyl–prolyl isomerase inhibitors. Bioorganic & Med. Chem. lett. vol. 4, pp. 315–320, 1994.*
Chemical Abstracts vol. 6, compound 704d (1966).
Pesson, Marcel et al., "Chemistry and Pharmacology of Derivatives of Pyrrole. I. 2–pyrrolyl Ketones. Preparation and Pharmacology." *Chim. Ther.* 3:127–36 (1966).
Archibald, John L. et al., "Reactions of Pyrroles. II. Preparation and Reactions of Pyrroleglyoxyloyl Derivatives", *J. Heterocycle Chem.* 4(3): 335–38 (1967).
Zellner, Hugo et al. "Reaction of Pyruvic Acid with O–diamine. III. Synthesis of 2–(A–oxoalkyl) benzimidazoles", *Monatsh. Chem.* 98 (3): 643–65 (1967).
Kost, A.N. et al. "Indole Chemistry. XXVII. 2–(Haloacetyl) indoles", *Khim. Geterotsikl. Soedin.*, 7(11): 1522–26 (1971).
Kotani, E. et al. "New Synthesis of the Alkaloid (±) –cryptoplleurine by Anodic Oxidation", *Tetrahedron* 30(17): 3027–30 (1974).
Barrett, Anthony, "A New Arrangement Reaction of Penicillin G Sulfoxide", *J. Chem. Soc., Perkin Trans.* 1(1): 170–75 (1979).

(List continued on next page.)

*Primary Examiner*—Charanjit S. Aulakh
(74) *Attorney, Agent, or Firm*—Gary M. Nath; Todd L. Juneau; Nahied K. Usman

(57) ABSTRACT

This invention relates to neurotrophic, low molecular weight, small molecule heterocyclic ketone and thioester compounds, compositions containing the same, and the use of such compounds for treating neurological disorders, including physically damaged nerves and neurodegenerative diseases.

75 Claims, 4 Drawing Sheets

U.S. PATENT DOCUMENTS

| | | |
|---|---|---|
| 4,053,599 | 10/1977 | Effland et al. . |
| 4,310,461 | 1/1982 | Krapcho et al. . |
| 4,374,829 | 2/1983 | Harris et al. . |
| 4,390,695 | 6/1983 | Krapcho et al. . |
| 4,531,964 | 7/1985 | Shimano et al. . |
| 4,575,079 | 3/1986 | Gavras et al. . |
| 4,578,474 | 3/1986 | Krapcho et al. . |
| 4,593,102 | 6/1986 | Shanklin, Jr. . |
| 4,766,110 | 8/1988 | Ryan et al. . |
| 4,808,573 | 2/1989 | Gold et al. . |
| 4,818,749 | 4/1989 | Gold et al. . |
| 4,912,128 | 3/1990 | Henning et al. . |
| 5,147,877 | 9/1992 | Goulet . |
| 5,166,317 | 11/1992 | Wallace et al. . |
| 5,192,773 | 3/1993 | Armistead et al. . |
| 5,215,969 | 6/1993 | Springer et al. . |
| 5,232,923 | 8/1993 | Fukazawa et al. . |
| 5,252,579 | 10/1993 | Skotnicki et al. . |
| 5,294,603 | 3/1994 | Rinehart . |
| 5,319,098 | 6/1994 | Burbaum et al. . |
| 5,321,041 | 6/1994 | Adachi et al. . |
| 5,330,993 | 7/1994 | Armistead et al. . |
| 5,359,138 | 10/1994 | Takeuchi et al. . |
| 5,385,918 | 1/1995 | Connell et al. . |
| 5,414,083 | 5/1995 | Hackl et al. . |
| 5,424,454 | 6/1995 | Burbaum et al. . |
| 5,447,915 | 9/1995 | Schreiber et al. . |
| 5,516,797 | 5/1996 | Armistead et al. . |
| 5,543,423 | 8/1996 | Zelle et al. . |
| 5,654,332 | 8/1997 | Armistead et al. . |
| 5,717,092 | 2/1998 | Armistead et al. . |
| 5,786,378 * | 7/1998 | Hamilton et al. ............ 514/423 |
| 5,990,131 * | 11/1999 | Hamilton et al. ............ 514/330 |
| 6,037,370 | 3/2000 | Armistead . |

OTHER PUBLICATIONS

Tressel, Roland et al., "Formation of Pyrroles, 2–pyrrolidones, and Pyridones by Heating of 4–aminobutyric Acid and Reducing Sugars", *J. Agric. Food Chem.* 41(11):2125–30 (1993).

Demirayak, Seref et al., "Synthesis of Some 1–(2–arylvinyl)–3–arylpyrazino [1,2–a] benzimidazole Derivatives and their Antimicrobial Activities", *Farmaco* 51(12): 825–27 (1996).

Askin, D. et al., "Efficient Degradation of FK–506 to a versatile synthetic intermediate," J. Org. Chem., 1990, 55(20), 5451–4.

Goulet, Mark T., and Boger, Joshua, "Degradative studies on the tricarbonyl containing macrolide rapamycin," Tetrahedron Lett., 1990, 31(34), 4845–8.

Jones, T. et al., "Chemistryof tricarbonyl hemiketals and application of Evans technology to the total synthesis of the immunosuppresant (–)–FK–506," J. Am. Chem. Soc., 1990, 112(8), 2998–3017.

Jones, A. et al., "A formal synthesis of FK–506. Exploration of some alternatives to macrolactamization," J. Org. Chem., 1990, 55(9), 2786–97.

Rao, A.V., et al., "Studies directed towards the synthesis of immunosuppresive agent FK–506: construction of the tricarbonyl moiety," Tetrahedron Lett., 1990, 31(10), 1439–42.

Harding, M.W., et al., "A receptor for the immunosuppresive FK506 is a cis–trans peptidyl–prolyl isomerase," Nature Lett., 1989, 341, 758–60.

Finberg, Robert W. et al., "Prevention of HIV–1 Infection and Preservation of CD4 Function by the Binding of CPFs to gp120," Science, 1990, 249, 287–91.

Goodfellow, Val S. et al., "p–Nitrophenyl 3–diazopyruvate and diazopyruvamide, a New Family of Photoactivatable Cross–Linking Bioprobes," Biochemistry, 28(15), 6346–60.

Wasserman, H.H. et al., "Synthesis of the tricarbonyl region of FK–506 through an amidophosphorane [Erratum to document cited in CA111(7):57366p]," J. Org. Chem., 1989, 54(22), 5406.

Wasserman, H.H. et al., "Synthesis of the tricarbonyl region of FK–506 through an amidosphere," J. Org. Chem., 1989, 54(12), 2785–6.

Dragovich et al., "Structured–Based Design of Novel, Urea–Containing FKBP12 Inhibitors," J. Med. Chem., 1996, 39, 1872–1884.

Gold et al., The Immunosuppressant FK506 Increases the Rate of Axonal Regeneration in Rat Sciatic Nerve, The Journal of Neuroscience, 1995, 15(11), 7509–7516.

Gold et al, "The Immunosuppressant FK506 increases functional recovery and nerve regeneration following peripheral nerve injury," Restorative Neurology and Neuroscience, 1994, 6, 287–296.

Lyons et al., "Immunosuppressant FK506 promotes neurite outgrowth in culture of PC12 cells and sensory ganglia," Proc. Natl. Acad. Sci. USA, 1994, 91, 3191–3195.

Gold, et al, "Multiple signals underlie the anatomy–induced up–regulation of c–JUN in adult sensory neurons," Neuroscience Letters 176, 1994, 123–127.

Gold et al., "Regulation of the transcription factor c–JUN by nerve growth factor in adult sensory neurons," Neuroscience Letters 154, 1993, 129–133.

Askin, D. et al., "Chemistry of FK–506: benzilic acid rearrangement of the tricarbonyl system," Tetrahedron Lett., 1989, 30(6), 671–4.

Coleman, R., and Danishefsky, S., "Degradation and manipulations of the immunosupressant FK506: preparation of potantial synthetic intemediates," Heterocycles, 1989, 28(1), 157–61.

Faelth, Lars et al., "Interactions between C=S groups in 1,2 and 1,3–bis(thiocarbonyl) Compounds: A Study by Spectroscopy, X–Ray Crystallography and CNDO/S Calculations," THEOCHEM, 1989, 55, 239–59.

Doulmedais, Ali et al., "Sterochimistry of Electrochemical Reduction of Optically Active –ketoamides. II. Electroreduction of benzoylformamides derived from S–(–)–proline," Bull. Soc. Chim. Fr., 1989, (2), 185–01. (French).

Soai, Kenso et al., "Asymmetric Allylation of –keto amides Derived from (S)–proline esters," Pept. Chem., 1986, 24, 327–30.

Munegumi, M. et al., "Asymmetric Catalytic Hydrogenations of N–pyruvoyl–(s)–proline esters," Bull. Chem. Soc. Jpn., 1987, 60(1), 243–53.

Soai, Kenso and Ishizaki, Miyuki, "Diasteroselective asymmetric allylation of chiral –keto amides with allyltrimethylsilane. Preparation of protected homoallylic alcohols," J. Chem. Soc., 1984, 15, 1016–17.

Soai, Kenso et al., "Sodium borohydride as diastereoselective reducing agent of chiral –keto amides," Pept. Chem., 1982, 20, 81–4.

Soai, Kenso and Ishizaki, Miyuki, "Asymmetric Synthesis of Functionalized tertiary alcohols by diastereoselective allylation of chiral –keto amides derived from (S)–proline esters: control of sterochemistry based on saturated coordination of Lewis acid," J. Org. Chem., 1986, 57(17) 3290–5. (English).

Soai, Kenso et al., "Asymmetric synthesis of both enantiomers of –hydroxy acids by the diastereoselective reduction of chiral –keto amides with complex metal hydrides in the presence of a metal salt," Chem. Lett., 1986, 11, 1897–900.

Soai, Kenso and Hasegawa, Hitoshi, "Diastereoselective reduction of chiral –ketoamides derived from (S)–proline esters with sodium borohydride. Preparation of optically active –hydroxy acids," J. Chem. Soc., 1985, 1(4), 769–72.

Bender, D., et al., "Periodate oxidation of –keto γ–lactams. Enol oxidation and β–lactam formation. Mechanism of periodate hydroxlation reactions," J. Org. Chem., 1978, 43(17), 3354–62.

Colombo, L. et al., "Enantioselective synthesis of secondary alcohols in the presence fo chiral ligands," Tetrahedron, 1982, 38(17), 2725–7.

Soai, Kenso et al., "Unusual effect of mixed solvent on the asymmetric reduction of chiral α–keto amides with sodium borohydride," J. Chem. Soc., 1982, 21, 1282–3.

Steglich, Wolfgang et al., "Activated carboxylic acid derivatives. II. A simple synthesis of 2–oxycarboxylic acid amides, N–(2–oxoacyl)amino acid esters and 2–oxocarboxylic acid hydrazides," Synthesis, 1978, 8, 622–4. (German).

Cushman, D.W. et al., "Design of potent competitive inhibitors of angiotensin–converting enzyme. Caboxylalkanoyl and mercaptoalkanoly amino acids," Biochemistry, 1977, 16(25), 5484–91.

Steglich, Wolfgang and Hinze, Sabine, "A rational synthesis of N–triluoroacetylamino acids," Synthesis, 1976, 8, 399–401. (German).

Bycroft, Barrie W., and Lee, Grahame R., "Efficient asymmetric synthesis of .alpha.–amino from .alpha.–keto acids and ammonia with conservation of the chrial reagent," J. Chem. Soc., 1975, 24, 988–9.

Chakaraborty, Tushar K., "Studies towards the development of cyclic peptide–based analogs of macrolide immunosuppresants," Pure Appl. Chem., 1996, 68(3), 565–568.

Ponticelli, Claudio, "Treatment of the Nephrotic Syndrome with Cyclosporin A," J. of Autoimmunity, 1992, 5, 315–24.

Tindall, Richard S.A., "Immunointervention with Cyclosporin A in autoimmune Neurological Disorders," J.of Autoimmunity, 1992, 5,301–313.

Tugwell, Peter, "Cyclosporin in the Treatment of Rheumatoid Arhtritis", J. of Autoimmunity, 1992, 5, 231–40.

Fry, Lionel, "Psoriasis: Immunopathology and Long–term Treatment with Cyclosporin," J. of Autoimmunity, 1992, 5, 277–83.

Feutran, Gilles, "The Optimal use of Cyclosporin o in Autoimmune Disease," J. of Autoimmunity, 1992, 5, 183–95.

Slee, Deborah H. et al., "Selectivity in the Inhibition of HIV and FIV Protease: Inhibitory and Mechanistic Studies of Pyrrolidine–Containing α–Keto Amide and Hydroxyethylamine Core Structures," J. Am. Chem. Soc., 1995, 117(48), 1187–78.

Nicolau, K.C. et al., "Total synthesis of rapamycin," Che.—Eur. J., 1995, 1(5), 318–33.

Munoz, Benito et al., "α–ketoamide Phe–Pro isostere as a new core structure for the inhibition of HIV protease," Bioorg. Med. Chem., 1994, 2(10), 1085–90.

Hauske, James R. et al., "Investigation of the effects of synthetic, non–cytotoxic immunophilin inhibitors on MDR," Bioorg. Med. Chem. Lett., 1994, 4(17), 2097–102.

Mashkovskii, M.D. et al., "1–[4–(2–Hydroxy–3–tert–butylaminopropoxy)–indole–3–yl (5–acetamido–1–(S)–carboxypentyl)–Dl–alanyl]–L–proline dihydrochloride, a new angiotensin–converting enzyme inhibitor with β–dihydrochloride, a new angiotensin–converting enzyme inhibitor with β–adrenoblocking properties," Khim.–Farm. Zh., 1993, 27(10), 16–20.

Ranganathan, Darshan et al., "Protein Backbone Modification by Novel Cα–C Side–Chain Scission," 1994, J. Am. Chem. Soc., 116(15), 6545–57.

Baader, Ekkehard et al., "Inhibition of prolyl 4–hydroxylase by oxalyl amino acid derivatives in vitro, in isolated microsomes and in embryonic chicken tissues," Biochem. J., 1994, 300(2), 525–30.

Holt, Dennis A. et al., "Structure–activity of synthetic FKBP ligands as peptidyl–prolyl isomerase inhibitors," Bioorg. Med. Chem. Lett., 1994, 4(2), 315–20.

Karle, Isabella L. et al., "Conformation of the oxalamide group in retro–bispeptides. Three crystal structures." Int. J. Pept. Protein Res., 1994, 43(2), 160–5.

Kaczmar, et al., "Darstellung verscheider Schlangenkafig–Polyelektrolyte auf der Basis von Polyacrylamiden und einem Anionenaustauscher," Makromol. Chem., 1976, 177, 1981–9. (German).

Steiner, Jospeh P. et al., "High brain densities of the immunophilin FKBP colocalized with calcineurin," Nature Lett., 1992, 358, 584–7.

Pattenden, Gerald and Tnkard, Mark, "Facile Synthesis of the tricarbonyl subunit in the immunosuppresant rapamycin," Tetrahedron Lett., 1993, 34(16), 2677–80.

Furber, M. et al., "Studies relating to the immnosuppressive activity of FK506," Tetrahedron Lett., 1993, 34(8), 1351–4.

Ranganathan, Darshan et al., "Oxalopeptides as core motifs for protein design," J. Chem. Soc., 1993, (1), 92–4.

Dawson, Ted M. et al. "Immunosuppresant FK506 enhances phosphorylation of nitric oxide synthase and protects against glutamate neurotoxicity," Proc. Natl. Acad. Sci. USA, 1993, 90, 9808–12.

Cunliffe, C. Jane et al., "Novel inhibitors of proplyl 4–hydroxylase. 3. Inhibition by the substrate analog N–oxaloglycine and its derivatives," J. Med. Chem., 1992, 35(14), 2552–8.

Waldmann, Herbert, "Amino acid esters as chiral auxilaries in Barbier–type reactions in aqueous solutions," Liebigs Ann. Chem., 1991, (12), 1317–22. (German).

Krit, N.A. et al., "Impact of the nature of alkyl radical on the biological activity of N–carboxyalkyl dipeptides," Khim.–Farm. Zh., 1991, 25(7), 44–6. (Russian).

Blaschke et al., Chemical Abstracts, 1974, 84, 78405k.

Caufield, Craig E. and Musser, John H., *Annual Reports in Medicinal Chemistry,* Johns (Ed.), Academic Press, Inc., Chapter 21, 195–204, 1989.

Effenberger F. et al., "Diastereoselective addition of benzenesulfenyl chloride to 1–acryloylproline esters," Chemical Abstracts, 1989, 10, 778–9.

Nakatsuta. M. et al. "Total Synthesis of FK506 and an FKBP Probe Reagent, ($C_8$, $C_{9-13}C_2$)–FK–506," J. Am. Chem. Soc., 1990, 112 (14), 5583–90.

Shu, A. et al., "Synthesis of I–125 labeled photoaffinity rapamycin analogs," J. Labelled Compd. Radiopharm., 1996, 38(3), 277–37.

Tatlock, J. et al., "High affinity FKBP–12 ligands from (R)–(–)–carvone. Synthesis and evaluation of FK506 pyranose ring replacements," Bioorg. Med. Chem. Lett., 1995, 5(21), 2489–94.

Teague, S. et al., "Synthesis of FK506–cyclosporin hybrid macrocycles," Bioorg. Med. Chem. Lett., 1995, 5(20), 2341–6.

Stocks, M. et al., "macrocyclic ring closures employing the intramolecular Heck reaction," Tetrahedron Lett., 1995, 36(36), 6555–8.

Wang, C.P. et al., "High performance liquid chromatographic isolation and spectroscopic characterization of three major metabolites from the plasma of rats receiving rapamycin (sirolimus) orally," J. Liq. Chromatogr., 1995, 18(13), 2559–68.

Armistead, D.M. et al., "Design, synthesis and structure of non–macrocyclic inhibitors of FKBP12, the major binding protein for the immunosuppressant FK506," Acta Crystallogr. 1995, D51(4), 522–8.

Luengo, J. et al., "Structure–activity studies of rapamycin analogs:evidence that the C–7 methoxy group is part of the effector domain and positioned at the FKBP:12–FRAP interface," Chem. Biol., 1995, 2(7), 471–81.

Furber, Mark, "FKBP–12–ligand–calceineurin interactions: analogs of SBL506," J. Am. Chem. Soc., 1995, 117(27), 7267–8.

Wang CP et al., "A high performace liquid chromatographic method for the determination of rapamycin (sirolamus) in the rat serum, plasma, and blood and in monkey serum," J. Liq. Chromatogr., 1995, 18(9), 1801–8.

Chakraborty, TK et al., "Design and Synthesis of a rapamycin–based high affinity binding FKBP12 ligand," Chem. Biol., 1995, (2)3, 157–61.

Smith, A.B. et al., "Total synthesis of rapamycin and demethoxyrapamycin," J. Am. Chem. Soc., 1995, 117(19), 5407–8.

Baumann, K. et al., "Synthesis and oxidative cleavage of the major equilibrium products of ascomycin and Fk 506," Tetrahedron Lett., 1995, 26(13), 2231–4.

Nelson, F. et al., "A novel ring contraction of rapamycin," Tetrahedron Lett., 1994, 35(41), 7557–60.

Dawson, T.M. et al., "The immunophilins, FK506 binding and cyclophilin, are discretely localized in the brain: relationship to calcineurin," Neuroscience, 1994, 62(2), 569–80.

Cameron, Andrew et al., "Immunophilin FK506 binding protein associated with inositol 1,4,5–triphosphate receptor modulates calcium flux," Proc. Natl. Acad. Sci. USA, 1995, 92, 1784–1788.

Stocks, M. et al., "The contribution to the binding of the pyranoside sustituents in the excised binding domain of FK–506," Bioorg. Med. Chem. Lett., 1994, 4(12), 1457–60.

Steiner, J.P. et al., "Nonimmunosuppressive Ligands for Neuroimmunophilins Promote Nerve Extension In Vitro and In Vivo," Soc. For Neuroscience Abstracts, 1996, 22, 297.13.

Lyons, W. Ernest et al., "Neronal Regeneration Enhances the Expression of the Immunophilin FKBP–12," The Journal of Neuroscience, 1995, 15, 2985–94.

Skotnicki, Jerauld et al., "Ring expanded rapamycin derivatives," Tetrahedron Lett., 1994, 35(2), 201–2.

Skotnicki, Jerauld et al., "Synthesis of secorapamycin esters and amides," Tetrah. Lett., 1994, 35(2), 197–200.

Rao, A.V. Rama and Desibhatla, Vidyanand, "Stuides directed towards the synthesis of rapamycin: stereoselective synthesis of C–1 to C–15 segment," Tetrahedron Lett., 1993, 34(44), 7111–14.

Andrus, Merrit B., "Structure–based design of an acyclic ligand that bridges FKBP12 and calcineurin," J. Am. Chem. Soc., 1993, 115(2), 10420–1.

Luengo, Juan I. et al., "Efficient removal of pipecolinate from rapamycin and FK506 by reaction with tetrabutylammonium cyanide," Tetrahedron Lett., 1993, 34(29), 4599–602.

Steffan, Robert J. et al., "Base catalyzed degradation of rapamycin," Tetrahedron Lett., 1993, 34(23), 3699–702.

Nicolau, K.C. et al., "Total Synthesis of rapamycin," J. Am. Chem. Soc., 1993, 115(10), 4419–20.

Hayward, C.M. et al., "Total synthesis of rapamycin via a novel titanium–mediated aldol macrocylization reaction," J. Am. Chem. Soc., 1993, 115(20), 9345–6.

Yohannes, Daniel et al. "Degradation of rapamycin: synthesis of a rapamycin–derived fragment containing the tricarbonyl and triene sectors," Tetrahedron Lett., 1993, 34(13), 2075–8.

Luengo, J. et al., "Studies on the chemistry of rapamycin: novel transformation under Lewis–acid catalysis," Tetrahedron Lett., 1993, 34(6), 991–4.

Yohannes, Daniel et al., "Degradation of rapamycin: retrieval of major intact subunits," Tetrahedron Lett., 1992, 33(49), 7469–72.

Hovarth, R. et al., "An application of the Evans–Prasad 1,3–Syn diol synthesis to a stereospecific synthesis of the $C_{10}$–$C_{27}$ segment of rapamycin," Tetrahedron Lett., 1993, 34(25), 3993–3996.

Whitesell, J.K. et al., "Asymmetric Induction. Reduction, Nucleophilic Addition to, the Ene Reactions of Chiral α–Ketoesters," J. Chem. Soc., Chem Commun., 1983, 802.

Ando, Takao et al., "Formation of Crossed Phenzine from the reaction between Tetra–p–anisyl– and Tetra–p–tolyl–hydrazines in Liquid Sulphur Dioxide," Chem. Comm., S. Chem. Commun., 1975, 989.

Kino, Toru et al., "FK–506, A novel immunosuppressant isolated from A Streptomyces," J. of Antibiotics, 1987, 40(9), 1249–55.

Goulet, Mark T. and Boger, Joshua, "Degradative studies on the tricarbonyl containing macrolide rapamycin," Tetrahedron Lett., 1991, 32(45), 6454.

Goulet, Mark T. et al., "Construction of the FK–506 analog from rapamycin–derived materials," Tetrahedron Lett., 1991, 32(36), 4627–30.

Rao, A.V. Rama et al., "Studies directed towards the synthesis of immunosuppressive agent FK–506: synthesis of the entire bottom half," Tetrahedron Lett., 1991, 32(9), 1251–4.

Fisher, Matthew et al., "On the remarkable propensity for carbon–carbon bond cleavage reactions in the C(8)–C(10) region of FK–506," J. Org. Chem., 1991, 56(8), 2900–7.

Linde, Robert G. et al., "Straightforward synthesis if 1,2,3–tricarbonyl systems," J. Org. Chem., 1991, 56(7), 2534–8.

Hayward, C.M. et al., "An application of the Suarez reation to the regiospecific synthesis of the $C_{28}$–$C_{42}$ segment of rapamycin,", 1993, 3989–92.

Waldmann, Herbert, "Proline benzyl ester as chiral auzilary in Barbier–type reactions in aqueous solution," 1990, Synlett, 10, 627–8.

Gold, Bruce G. et al., "Regulation of aberrant neurofilament phosophorylation in neuronal periokarya. IV. Evidence for the involvement of two signals," *Brain Search*, 626 (1993) 23–30.

Hauske, James R. et al., "Design and Synthesis of Novel FKBP Inhibitors," J. Med. Chem., 1992, 35, pp. 4284–4296.

Holt, Dennis A. et al., "Structure Acitivity Studies of Non-macrocyclic Rapamycin Derivatives," Bioorganic & Medical Chemistry Letters, 1993, vol. 3, No. 10, pp. 1977–1980.

Yamashita, Dennis S. et al., "Design Synthesis and Evaluation of Dual Domain FKBP Ligands," Bioorganic & Medicinal Chemistry Letters, 1994, vol. 3, No. 2, pp. 325–28.

Teague, Simon J. et al., "Synthesis and Study of a Non Macrocyclic FK506 Derivative," Bioorganic & Medicinal Chemistry Letters, 1994, vol. 4, No. 13, pp. 1581–1584.

Luengo, Juan I. et al. "Synthesis and Structure–Activity Relationships of Macrocyclic FKBP Ligands," Bioorganic & Medicinal Chemistry Letters, 1994, vol. 4, No. 2, pp. 321–324.

Holt, Dennis A. et al., "Structure–Activity Studies of Synthetic FKBP Ligands as Prptidyl–Prolyl Isomerase Inhibitors," Bioorganic & Medicinal Chemistry Letters, 1994, vol. 4, No. 2, pp. 315–320.

Teague, Simon J. et al. "The Affinity of the Excised Binding Domain of the FK–506 for the Immunophilin FKBP12," Bioorganic & Medicinal Chemistry Letters, 1993, vol. 3, No. 10, pp. 1947–1950.

Caffrey, Moya V. et al. "Synthesis and Evaluation of Dual Domain Macrocyclic FKBP12 Ligands," Bioorganic & Medicinal Chemistry Letters, 1994, vol. 4, No. 21, pp. 2507–2510.

Birkenshaw, Timothy N. et al. "Synthesis FKBP12 Ligands. Design and Synthesis of Pyranose Replacements," Bioorganic & Medicinal Chemsitry Letters, 1994, vol. 4, No. 21, pp. 2501–2506.

Holt, Dennis A. et al. "Design, Synthesis, and Kinetic Evaluation of High–Affinity FKBP Ligands and the X–ray Crystal Structures of their Complexes with FKBP12", J. Am. Chem. Soc., 1993, 115, pp. 9925–9938.

Wang, Gary T. et al. "Synthesis and FKBP Binding of Small Molecule Mimics of the Tricarbonyl Region of FK506," Bioorganic & Medicinal Chemistry Letters, 1994, vol. 4, No. 9, pp. 1161–1166.

Snyder, Solomon H. and Sabatini, David M., "Immunophilins and the Nervous System," Nature Medicine, 1995, vol. 1, No. 1, pp. 32–37.

Egbertson, M., and Danishefsky, S., "A synthetic route to the tricarbonyl region of FK–506," J. Org. Chem., 1989, 54(1), 11–12.

Williams, D.R. and Benbow, J.W., "Synthesis of the $\alpha,\beta$ diketo amide segment of the novel immunosuppresive FK506," J. Org. Chem., 1988, 53(191), 4643–4.

Kocienski, P. et al., "A synthesis of the C(1)–C(15) segemnt of tsukubaenolide (FK506)," Tetrahedron Lett., 1988, 29(35), 4481–4.

Tanaka, H. et al., "Structure of FK506, a novel immunosuppressant isolated from Streptomyces," J. Am. Chem. Soc., 1987, 109(16), 5031–3.

Marshall, J.A. et al., "Convenient synthesis of dioxopiperazines via aminolysis of .alpha.–(pyruvylamine) esters," Synth. Commun., 1975, 5(3), 237–44.

Stocks, Michael J. et al. "The Contriction to Binding of the Pyranoside Substituents in the Excised Binding Domain of FK–506," Bioorganic & Medicinal Chemistry Letters, 1994, vol. 4, No. 12, pp. 1457–1460.

Haeusler, Johannes and Schmidt, Ulrich, "Amino acids and peptides. IX. Pyruvoyl amino acids," Chem. Ber., 1974, 107(1), 145–51. (German).

Hearn, Walter R., and Worthington, Robert E., "L–Proline–N–oxalic anhydride," J. Org. Chem., 1967, 32(12), 4072–4.

* cited by examiner

HETEROCYCLIC KETONE AND THIOESTER COMPOUNDS AND USES

This application is a continuation-in-part of U.S. patent application Ser. No. 08/904,461, filed Aug. 1, 1997 now U.S. Pat. No. 5,990,131, which is in turn a continuation-in-part of U.S. patent application Ser. No. 08/721,765, filed Sep. 25, 1996, now U.S. Pat. No. 5,786,378, the entire contents of which are considered a part of this application and are hereby incorporated by reference.

BACKGROUND OF THE INVENTION

This invention relates to neurotrophic, low molecular weight, small molecule heterocyclic ketone and thioester compounds, and their use for effecting neuronal activities in animals, including treating neurological disorders.

It has been found that picomolar concentrations of an immunosuppressant, such as FK506 or rapamycin, stimulates neurite outgrowth in PC12 cells and sensory neurons, namely dorsal root ganglion cells (DRGs). Lyons et al., *Proc. of Natl. Acad. Sci.*, 1994, vol. 91, pp. 3191–3195. In whole animal experiments, FK506 has been shown to stimulate nerve regeneration following facial nerve injury and results in functional recovery in animals with sciatic nerve lesions.

Studies have demonstrated that neurodegenerative disorders, such as senile dementia of the Alzheimer's type (SDAT or Alzheimer's disease), Parkinson's disease and amyotrophic lateral sclerosis (ALS), may occur due to the loss, or decreased availability, of a neurotrophic substance specific for a particular population of neurons affected in the disorder. Several neurotrophic factors affecting specific neuronal populations in the central nervous system have been identified.

For example, it has been hypothesized that Alzheimer's disease results from a decrease or loss of nerve growth factor (NGF). It has thus been proposed to treat SDAT patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects, including nephrotoxicity, such as impairment of glomerular filtration and irreversible interstitial fibrosis (Kopp et al., *J. Am. Soc. Nephrol.*, 1991, 1:162); neurological deficits, such as involuntary tremors, or non-specific cerebral angina, such as non-localized headaches (De Groen et al., *N. Engl. J. Med.*, 1987, 317:861); and vascular hypertension, with complications resulting therefrom (Kahan et al., *N. Engl. J. Med.*, 1989, 321:1725).

To avoid the drawbacks associated with use of large molecule proteins and/or immunosuppressants, the present invention provides small molecule compounds for enhancing neurite outgrowth, and promoting neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, Huntington's Disease, SDAT (Alzheimer's disease) and amyotrophic lateral sclerosis (ALS).

SUMMARY OF THE INVENTION

The present invention relates to neurotrophic, low molecular weight, small molecule heterocyclic ketone or thioester compounds. In a preferred embodiment, the compounds are non-immunosuppressive. In another preferred embodiment, the compounds of the present invention have an affinity for FKBP-type immunophilins, such as FKBP12; and affinity binding or interaction may inhibit the prolyl-peptidyl cis-trans isomerase, or rotamase, activity of the binding protein.

The present invention also relates to a pharmaceutical composition comprising:
(i) an effective amount of a neurotrophic, low molecular weight, small molecule heterocyclic ketone or thioester compound; and
(ii) a pharmaceutically acceptable carrier.

The present invention further relates to a method of effecting a neuronal activity in an animal, comprising administering to said animal an effective amount of a neurotrophic, low molecular weight, small molecule heterocyclic ketone or thioester compound.

Specifically, the present invention relates to a compound of formula II:

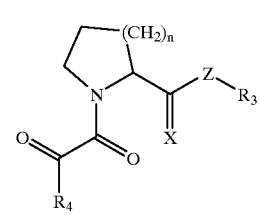

or a pharmaceutically acceptable salt, ester, or solvate thereof, wherein:

n is 1 or 2;

X is O or S;

Z is selected from the group consisting of S, $CH_2$, $CHR_1$, $CR_1R_2$, and a bond;

$R_1$, $R_2$, and $R_3$ are independently selected from the group consisting of $C_1$–$C_5$ straight or branched chain alkyl, $C_2$–$C_5$ straight or branched chain alkenyl, and Ar, wherein said $R_1$, $R_2$, or $R_3$ is unsubstituted or substituted with one or more halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

$R_4$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, and Ar; and Ar is aryl.

The present invention also relates to a pharmaceutical composition comprising:
(i) an effective amount of the compound of formula II; and
(ii) a pharmaceutically acceptable carrier.

The present invention further relates to a method of effecting a neuronal activity in an animal, comprising administering to said animal an effective amount of a compound of formula II.

DETAILED DESCRIPTION OF THE INVENTION

Definitions

Figure 1:
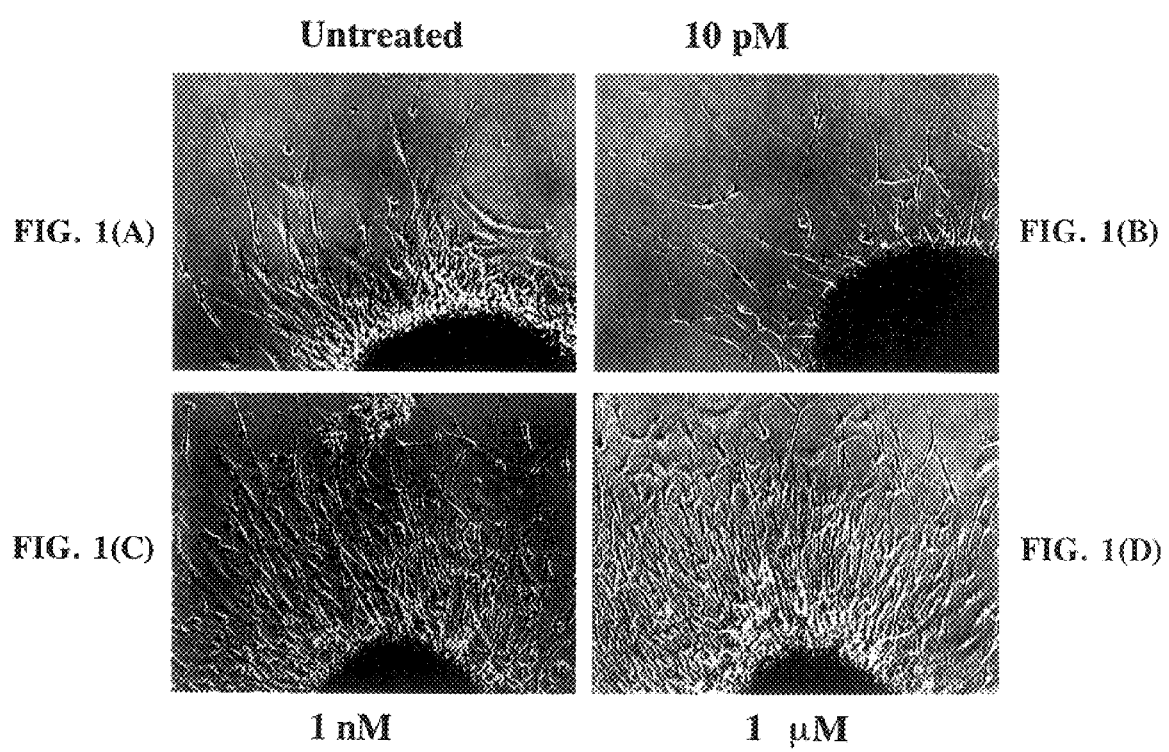
FIG. 1(A) is a representative photomicrograph of untreated sensory neurons.
FIG. 1(B) is a representative photomicrograph of compound 1 (10 pM) promoting neurite outgrowth in sensory neurons.
FIG. 1(C) is a representative photomicrograph of compound 1 (1 nM) promoting neurite outgrowth in sensory neurons.
FIG. 1(D) is a representative photomicrograph of compound 1 (1 μM) promoting neurite outgrowth in sensory neurons.
Figure 2:
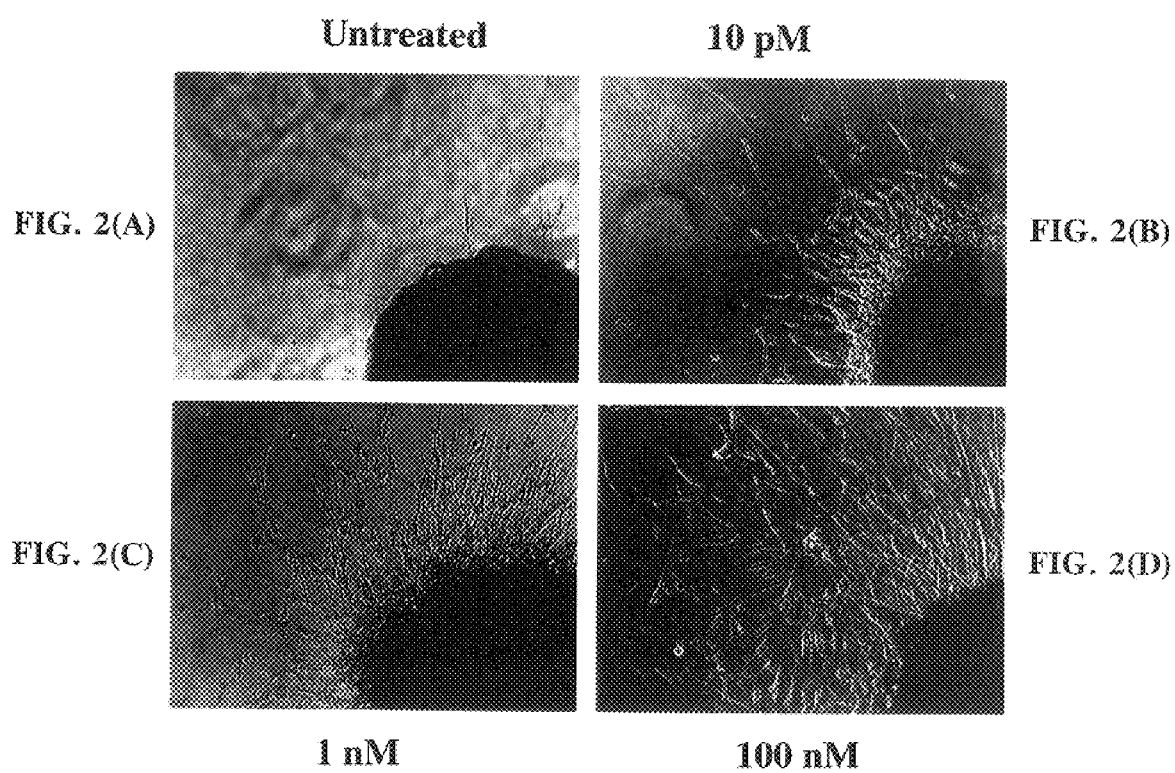
FIG. 2(A) is a representative photomicrograph of untreated sensory neurons.
FIG. 2(B) is a representative photomicrograph of a related compound, 2-Phenyl-1-ethyl (2S)-1-(3,3-dimethyl-1,2-dioxopentyl)-2-pyrrolidinecarbothioate, (10 pM) promoting neurite outgrowth in sensory neurons.
FIG. 2(C) is a representative photomicrograph of a related compound, 2-Phenyl-1-ethyl (2S)-1-(3,3-dimethyl-1,2-dioxopentyl)-2-pyrrolidinecarbothioate, (1 nM) promoting neurite outgrowth in sensory neurons.
FIG. 2(D) is a representative photomicrograph of a related compound, 2-Phenyl-1-ethyl (2S)-1-(3,3-dimethyl-1,2-dioxopentyl)-2-pyrrolidinecarbothioate, (100 nM) promoting neurite outgrowth in sensory neurons.
Figure 3:
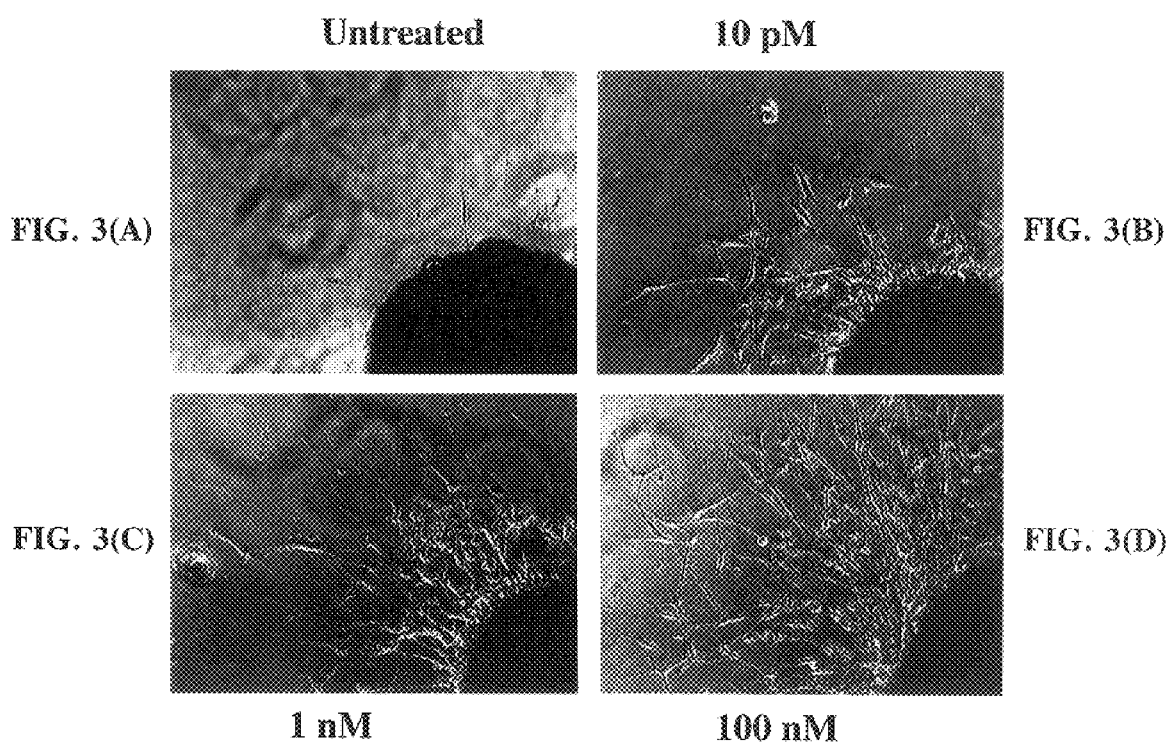
FIG. 3(A) is a representative photomicrograph of untreated sensory neurons.
FIG. 3(B) is a representative photomicrograph of a related compound, 2-Phenyl-1-ethyl 1-(3,3-dimethyl-1,2-dioxopentyl)-2-piperidinecarbothioate, (10 pM) promoting neurite outgrowth in sensory neurons.
FIG. 3(C) is a representative photomicrograph of a related compound, 2-Phenyl-1-ethyl 1-(3,3-dimethyl-1,2-dioxopentyl)-2-piperidinecarbothioate, (1 nM) promoting neurite outgrowth in sensory neurons.
FIG. 3(D) is a representative photomicrograph of a related compound, 2-Phenyl-1-ethyl 1-(3,3-dimethyl-1,2-dioxopentyl)-2-piperidinecarbothioate, (100 nM) promoting neurite outgrowth in sensory neurons.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like. It is also contemplated as within the scope of the present invention that "alkenyl" may also refer to an unsaturated hydrocarbon chain wherein any of the carbon atoms of said alkenyl are optionally replaced with O, NH, S, or $SO_2$. For example, carbon 2 of 4-pentene can be replaced with O to form (2-propene)oxymethyl.

"Alkoxy" refers to the group —OR wherein R is alkyl as herein defined. Preferably, R is a branched or unbranched saturated hydrocarbon chain containing 1 to 6 carbon atoms.

"Alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like. It is also contemplated as within the scope of the present invention that "alkyl" may also refer to a hydrocarbon chain wherein any of the carbon atoms of said alkyl are optionally replaced with O, NH, S, or $SO_2$. For example, carbon 2 of n-pentyl can be replaced with O to form propyloxymethyl.

Throughout this application, "R" or "$R_n$", where n is a number, is used to designate various substituents. These R groups are independently selected. Thus, for example, the fact that $R_1$ may be a branched alkyl in one context does not require that $R_1$ be the same branched alkyl, and does not prohibit that $R_1$ be, for example, a straight chain alkenyl in another context in the same molecule. It is intended that all "$R_n$" are selected independently of all other "$R_n$", whether or not the term "independently selected" is used.

"Aryl" or "aromatic" refers to an aromatic carbocyclic or heterocyclic group having a single ring, for example a phenyl ring; multiple rings, for example biphenyl; or multiple condensed rings in which at least one ring is aromatic, for example naphthyl, 1,2,3,4-tetrahydronaphthyl, anthryl, or phenanthryl. The ring(s) of an aryl moiety can be unsubstituted or substituted with one or more substituents including, but not limited to, halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; a heterocyclic ring may contain 1–6 heteroatom(s) selected from the group consisting of O, N, and S. The substituents attached to a phenyl ring portion of an aryl moiety in the compounds of the invention may be configured in the ortho-, meta-, or para-orientation(s), with the para-orientation being preferred.

Examples of typical aryl moieties included in the scope of the present invention may include, but are not limited to, the following:

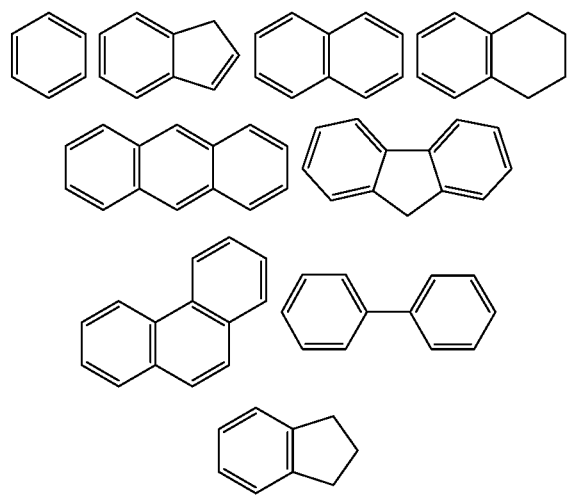

It should be kept in mind that, throughout this application, "Ar" or "$Ar_n$", where n is a number, is used to designate various substituents. As indicated throughout, these Ar groups are independently selected. Thus, for example, the fact that Ar may be phenyl in one context does not require that Ar be phenyl, nor prohibit that Ar be, for example, pyridyl in another context in the same molecule. It is intended that all "Ar" are selected independently of all other "Ar", whether or not the term "independently selected" is used.

"Carbocycle" or "carbocyclic" refers to an organic cyclic moiety in which the cyclic skeleton is comprised of only carbon atoms, whereas the term "heterocycle" or "heterocyclic" refers to an organic cyclic moiety in which the cyclic skeleton contains one or more heteroatoms selected from nitrogen, oxygen, or sulfur, and which may or may not include carbon atoms. The term "carbocycle" refers to a carbocyclic moiety containing the indicated number of carbon atoms. The term "$C_3$–$C_8$ cycloalkyl", therefore, refers to an organic cyclic substituent in which three to eight carbon atoms form a three, four, five, six, seven, or eight-membered ring, including, for example, a cyclopropyl, cyclobutyl, cyclopentyl, cyclohexyl, cycloheptyl, or cyclooctyl ring.

"Carbocyclic" or "heterocyclic" each includes within its scope a single ring system, multiple fused rings (for example, bicyclic, tricyclic, or other similar bridged ring systems or substituents, e.g. adamantyl) or multiple condensed ring systems. One skilled in the art, therefore, will appreciate that in the context of the present invention, a cyclic structure may comprise bi-, or tri-, or multiple condensed rings, bridged ring systems, or combinations thereof.

"Halo" refers to fluoro, chloro, bromo or iodo, unless otherwise indicated.

"Heterocycle" or "heterocyclic", refers to a saturated, unsaturated, or aromatic carbocyclic group having a single ring, multiple fused rings (for example, bicyclic, tricyclic, or other similar bridged ring systems or substituents), or multiple condensed rings, and having at least one heteroatom such as nitrogen, oxygen, or sulfur within at least one of the rings. This term also includes "Heteroaryl," which refers to a heterocycle in which at least one ring is aromatic. Any heterocyclic or heteroaryl group can be unsubstituted or optionally substituted with one or more groups, as defined above. Further, bi- or tricyclic heteroaryl moieties may comprise at least one ring which is either completely or partially saturated.

As one skilled in the art will appreciate, such heterocyclic moieties may exist in several isomeric forms, all of which are encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the present invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

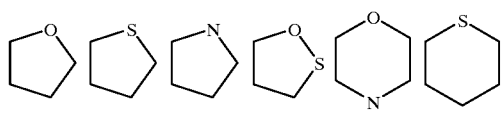

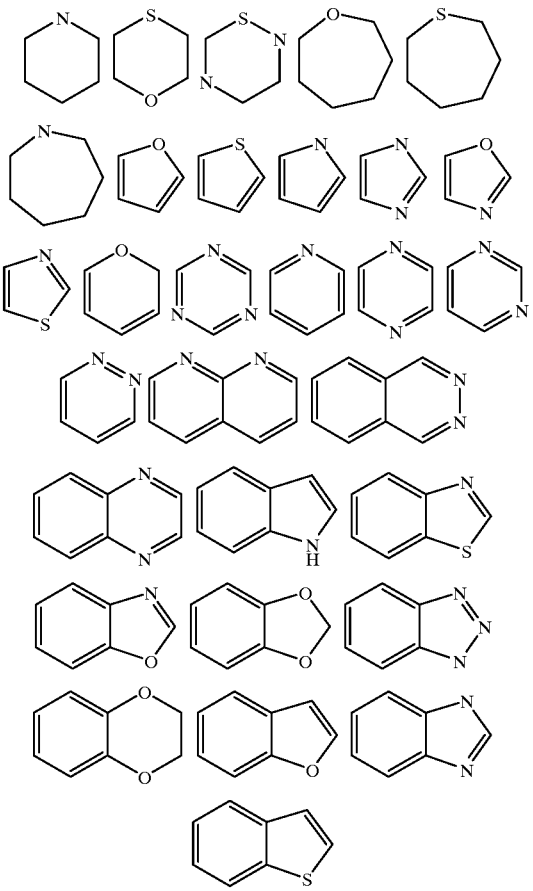

"Isomers" are different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Low molecular weight, small molecule compounds" include, without limitation, molecules which are smaller in size, molecular weight, or both in relation to the compounds Rapamycin, Cyclosporin, and FK506.

"Neurotrophic" includes without limitation the ability to stimulate neuronal regeneration or growth, the ability to prevent or treat neurodegeneration, or both.

"Non-immunosuppressive" refers to the inability of the compounds of the present invention to suppress an immune response when compared to a control such as FK506 or cyclosporin A. Assays for determining immunosuppression are well known to those of ordinary skill in the art. Specific, non-limiting examples of well known assays include PMA and OKT3, wherein mitogens are used to stimulate proliferation of human peripheral blood lymphocytes (PBC) and the tested compounds are evaluated on their ability to inhibit such proliferation.

"Pharmaceutically acceptable carrier" refers to any carrier, diluent, excipient, suspending agent, lubricating agent, adjuvant, vehicle, delivery system, emulsifier, disintegrant, absorbant, preservative, surfactant, colorant, flavorant, or sweetener. For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal, and intracranial injection or infusion techniques.

"Pharmaceutically acceptable salt", refers to an organic or inorganic salt which is useful in the treatment of a warm-blooded animal in need thereof. Such salts can be acid or basic addition salts, depending on the nature of the inventive compound to be used.

In the case of an acidic moiety in an inventive compound, a salt may be formed by treatment of the inventive compound with a basic compound, particularly an inorganic base. Preferred inorganic salts are those formed with alkali and alkaline earth metals such as lithium, sodium, potassium, barium, and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and like salts. Other salts of acidic moieties may include, for example, those salts formed with procaine, quinine and N-methylglucosamine, plus salts formed with basic amino acids such as glycine, ornithine, histidine, phenylglycine, lysine and arginine. Other suitable base salts, esters, or solvates include magnesium salts; salts with organic bases, such as dicyclohexylamine salts; and N-methyl-D-glucamine. An especially preferred salt is a sodium or potassium salt of an inventive compound.

With respect to basic moieties, a salt is formed by the treatment of the desired inventive compound with an acidic compound, particularly an inorganic acid. Preferred inorganic salts of this type may include, for example, hydrochloric, hydrobromic, hydroiodic, sulfuric, phosphoric, or like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, para-toluenesulfonic, sorbic, puric, benzoic, cinnamic, and like organic acids. Other suitable acids are adipate, alginate, aspartate, benzenesulfonate, bisulfate, butyrate, camphorsulfonate, cyclopentanepropionate, digluconate, dodecylsulfate, ethanesulfonate, glucoheptanoate, glycerophosphate, hemisulfate, heptanoate, hexanoate, 2-hydroxyethanesulfonate, methanesulfonate, naphthylate, 2-naphthalenesulfonate, nicotinate, oxalate, thiocyanate, tosylate, and undecanoate. An especially preferred salt of this type is a hydrochloride or sulfate salt of the desired inventive compound. Also, the basic nitrogen-containing groups can be quarternized with such agents as: 1) lower alkyl halides, such as methyl, ethyl, propyl, and butyl chlorides, bromides, and iodides; 2) dialkyl sulfates like dimethyl, diethyl, dibutyl, and diamyl sulfates; 3) long chain alkyls such as decyl, lauryl, myristyl, and stearyl substituted with one or more halide such as chloride, bromide, and iodide; and 4) aralkyl halides like benzyl and phenethyl bromide and others.

Also encompassed in the scope of the present invention are pharmaceutically acceptable esters of a carboxylic acid or hydroxyl containing group, including a metabolically labile ester or a prodrug form of an inventive compound. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as, for example, metabolism by enzymatic or hydrolytic cleavage. Esters of an inventive compound may include, for example, methyl, ethyl, propyl, and butyl esters, as well as other suitable esters formed between an acidic moiety and a hydroxyl containing moiety. Metabolically labile esters may include, for example, methoxymethyl, ethoxymethyl, iso-propoxymethyl, α-methoxyethyl, and groups such as α-(($C_1$–$C_4$)alkyloxy)ethyl; methoxyethyl, ethoxyethyl, propoxyethyl, and iso-propoxyethyl; 2-oxo-1,3-dioxolen-4-ylmethyl groups, such as 5-methyl-2-oxo-1,3,dioxolen-4-ylmethyl; $C_1$–$C_3$ alkylthiomethyl groups, for example, methylthiomethyl, ethylthiomethyl, isopropylthiomethyl; acyloxymethyl groups, for example, pivaloyloxymethyl, α-acetoxymethyl; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts, esters, or solvates. All of such forms likewise are to be construed as falling within the scope of the invention.

"Phenyl" refers to any possible isomeric phenyl radical, optionally monosubstituted or multisubstituted with substituents selected from the group consisting of alkyl, alkoxy, hydroxy, halo, and haloalkyl.

"Preventing neurodegeneration" includes (1) the ability to inhibit or prevent neurodegeneration in patients newly diagnosed as having a neurodegenerative disease or at risk of developing a new neurodegenerative disease and (2) the ability to inhibit or prevent further neurodegeneration in patients who are already suffering from, or have symptoms of, a neurodegenerative disease.

"Treating" or "treatment" covers any treatment of a disease, a condition, or both in an animal, particularly a human, and includes:

(i) preventing a disease or condition from occurring in a subject which may be predisposed to the disease or condition but has not yet been diagnosed as having it;

(ii) inhibiting a disease or condition, i.e., arresting its development; or (iii) relieving a disease or condition, i.e., causing regression of the disease or condition.

"Warm-blooded animal" or "animal" includes a mammal, including a member of the human, equine, porcine, bovine, murine, canine, or feline species. In the case of a human, the term "warm-blooded animal" or "animal" may also be referred to as a "patient". Further, as used herein, "a warm blooded animal in need thereof" refers to a warm-blooded animal which is susceptible to a disorder due to genetic or environmental conditions or predispositions. This term also refers to a warm blooded animal which has already suffered some degree of injury or damage because of genetic or environmental conditions to which the animal has been exposed or to which it is or was predisposed. Environmental conditions can include treatment with a therapeutic compound, as well as other types of injury or insult.

Compounds of the Invention

The present invention relates to low molecular weight, small molecule neurotrophic compounds. In a preferred embodiment, the compounds of the present invention do not exert any significant immunosuppressive activity. In another preferred embodiment, the compounds of the present invention may bind to, or otherwise interact with, FKBP-type immunophilins, such as FKBP12; such binding or interaction may inhibit the prolyl-peptidyl cis-trans isomerase, or rotamase, activity of the binding protein.

In another preferred embodiment, the compound of the present invention has a molecular weight no more than about 800 daltons. In a more preferred embodiment, the compound of the present invention has a molecular weight no more than about 500 daltons. In a particularly preferred embodiment, the compound of the present invention has a molecular weight no more than about 330 daltons.

In another preferred embodiment, the compound of the present invention exhibits a Chick Dorsal Root Ganglion Neurite Outgrowth Assay ("DRG") $ED_{50}$ value which is less than about 10 nM. In a more preferred embodiment, the compound of the present invention exhibits a DRG $ED_{50}$ value which is less than about 1.0 nM. In a particularly preferred embodiment, the compound of the present invention exhibits a DRG $ED_{50}$ value which is less than about 0.1 nM.

In another preferred embodiment, the compound of the present invention exhibits an MPTP Assay value which is greater than about 20% recovery of TH-stained dopaminergic neurons. In a more preferred embodiment, the compound of the present invention exhibits an MPTP Assay value which is greater than about 35% recovery of TH-stained dopaminergic neurons. In a particularly preferred embodiment, the compound of the present invention exhibits an MPTP Assay value which is greater than about 50% recovery of TH-stained dopaminergic neurons.

FORMULA I

A preferred embodiment of this invention is a compound of formula I:

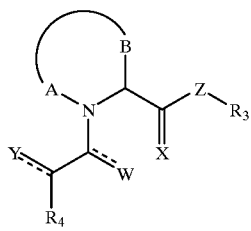

I or a pharmaceutically acceptable salt, ester, or solvate thereof, wherein:

A and B, together with the nitrogen and carbon atoms to which they are respectively attached, form a 5–7 membered saturated or unsaturated heterocyclic ring containing any combination of $CH_2$, O, S, SO, $SO_2$, NH, or $NR_4$ in any chemically stable oxidation state;

X is either O or S;

Z is either S, $CH_2$, $CHR_1$, $CR_1R_2$, or a bond;

W and Y are independently O, S, $CH_2$, or $H_2$;

$R_1$, $R_2$, and $R_3$ are independently $C_1$–$C_6$ straight or branched chain alkyl or alkenyl, which is substituted in one or more positions with $(Ar_1)_n$, $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_8$ straight or branched chain alkyl or alkenyl, or $Ar_2$;

n is 1 or 2;

$R_4$ is either $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, or hydroxyl; and $Ar_1$ and $Ar_2$ are each, independently, an aryl group. A preferred embodiment of an aryl group is a mono-, bi- or tricyclic, carbo- or heterocyclic ring, wherein the ring is either unsubstituted or substituted in one or more position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, or amino; wherein the individual ring sizes are 5–6 members; and wherein the heterocyclic ring contains 1–6 heteroatom(s) selected from the group consisting of O, N, and S.

Suitable mono- and bicyclic, carbo- and heterocyclic rings include, without limitation, naphthyl, indolyl, thioindolyl, furyl, thiazolyl, thienyl, pyridyl, quinolinyl, isoquinolinyl, fluorenyl, phenyl, and benzyl.

FORMULA II

Another preferred embodiment of this invention is a compound of formula II:

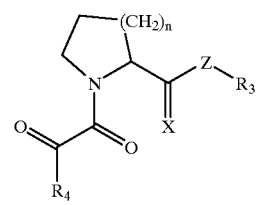

II or a pharmaceutically acceptable salt, ester, or solvate thereof, wherein:

n is 1 or 2;

X is O or S;

Z is selected from the group consisting of S, $CH_2$, $CHR_1$, $CR_1R_2$ and a bond;

$R_1$, $R_2$, and $R_3$ are independently selected from the group consisting of $C_1$–$C_5$ straight or branched chain alkyl, $C_2$–$C_5$ straight or branched chain alkenyl, and Ar, wherein said $R_1$, $R_2$, or $R_3$ is unsubstituted or substituted with one or more halo, trifluorormethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, or Ar;

$R_4$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, and Ar; and Ar is aryl. A preferred embodiment for Ar is phenyl, benzyl, pyridyl, fluorenyl, thioindolyl, or naphthyl, wherein said Ar is unsubstituted or substituted with one or more substituents independently selected from the group consisting of halo, trifluoromethyl, hydroxy, nitro, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino.

A particularly preferred embodiment of Formula II is a compound wherein n is 1, X is O, Z is $CH_2$, $R_3$ is 3-pyridylpropyl, and $R_4$ is 1,1-dimethylpropyl.

Another particularly preferred embodiment of Formula II is a compound wherein n is 2, X is O, Z is $CH_2$, $R_3$ is 4-phenylbutyl, and $R_4$ is 1,1-dimethylpropyl.

Another particularly preferred embodiment of Formula II is a compound wherein n is 1, X is O, Z is $CH_2$, $R_3$ is 2-phenylethyl, and $R_4$ is tert-butyl.

Another particularly preferred embodiment of Formula II is a compound wherein n is 1, X is O, Z is $CH_2$, $R_3$ is 3-(4-hydroxyphenyl)propyl, and $R_4$ is 1,1-dimethylpropyl.

The most preferred embodiments of Formula II are (2S)-3,3-dimethyl-1-[2-(5-(3-pyridyl)pyrrolidinyl]pentane-1,2-dione; 2-({1-oxo-6-phenyl}hexyl)(2S)-1-(3,3-dimethyl-1,2-dioxopentyl)piperidine; 2-(1-Oxo-4-phenyl)-butyl-1-(3,3-dimethyl-1,2-dioxobutyl)pyrrolidine; and (2S)-3,3-dimethyl-1-[2-(5-(4-hydroxyphenyl)pentanoyl) pyyrolidinyl]pentane-1,2-dione.

Specific examples of the embodiments of Formula II are presented in TABLE I. The molecular weights of the specifically exemplified compounds is between about 330 daltons and about 500 daltons.

TABLE I

| No. | n | X | Z | $R_3$ | $R_4$ |
|---|---|---|---|---|---|
| 1 | 1 | O | $CH_2$ | 3-Phenylpropyl | 1,1-Dimethylpropyl |
| 2 | 1 | O | $CH_2$ | 3-(3-Pyridyl)propyl | 1,1-Dimethylpropyl |
| 3 | 1 | O | $CH_2$ | 3-Phenylpropyl | tert-Butyl |
| 4 | 1 | O | $CH_2$ | 3-(3-Pyridyl)propyl | tert-Butyl |
| 5 | 1 | O | $CH_2$ | 3-(3-Pyridyl)propyl | Cyclohexyl |
| 6 | 1 | O | $CH_2$ | 3-(3-Pyridyl)propyl | Cyclopentyl |
| 7 | 1 | O | $CH_2$ | 3-(3-Pyridyl)propyl | Cycloheptyl |
| 8 | 1 | O | $CH_2$ | 2-(9-Fluorenyl)ethyl | 1,1-Dimethylpropyl |
| 9 | 1 | O | S | 2-Phenethyl | 1,1-Dimethylpropyl |
| 10 | 2 | O | S | 2-Phenethyl | 1,1-Dimethylpropyl |
| 11 | 1 | O | S | Methyl(2-thioindole) | 1,1-Dimethylpropyl |
| 12 | 1 | O | S | 2-Phenethyl | Cyclohexyl |
| 13 | 2 | O | S | 2-Phenethyl | tert-Butyl |
| 14 | 2 | O | S | 2-Phenethyl | Phenyl |
| 15 | 1 | O | $CH_2$ | 3-(4-Methoxyphenyl)propyl | 1,1-Dimethylpropyl |
| 16 | 2 | O | $CH_2$ | 4-(4-Methoxyphenyl)butyl | 1,1-Dimethylpropyl |
| 17 | 2 | O | $CH_2$ | 4-Phenylbutyl | 1,1-Dimethylpropyl |
| 18 | 2 | O | $CH_2$ | 4-Phenylbutyl | Phenyl |
| 19 | 2 | O | $CH_2$ | 4-Phenylbutyl | tert-Butyl |
| 20 | 1 | S | $CH_2$ | 3-Phenylpropyl | 1,1-Dimethylpropyl |
| 21 | 1 | S | S | 2-Phenethyl | 1,1-Dimethylpropyl |
| 22 | 2 | S | $CH_2$ | 3-Phenylpropyl | 1,1-Dimethylpropyl |
| 23 | 2 | S | S | 2-Phenethyl | 1,1-Dimethylpropyl |
| 24 | 1 | O | S | 2-Phenethyl | Cyclopentyl |
| 25 | 2 | O | S | 3-Phenylpropyl | tert-Butyl |
| 26 | 1 | O | S | 3-Phenylpropyl | 1,1-Dimethylpropyl |
| 27 | 1 | O | S | 3-(3-Pyridyl)propyl | 1,1-Dimethylpropyl |
| 28 | 1 | O | S | 3-Phenylpropyl | Cyclohexyl |
| 29 | 1 | O | S | 4-Phenylbutyl | Cyclohexyl |
| 30 | 1 | O | S | 4-Phenylbutyl | 1,1-Dimethylpropyl |
| 31 | 1 | O | S | 3-(3-Pyridyl)propyl | Cyclohexyl |
| 32 | 1 | O | S | 3,3-Diphenylpropyl | 1,1-Dimethylpropyl |
| 33 | 1 | O | S | 3,3-Diphenylpropyl | Cyclohexyl |
| 34 | 1 | O | S | 3-(4-Methoxyphenyl)propyl | 1,1-Dimethylpropyl |
| 35 | 2 | O | S | 4-Phenylbutyl | tert-Butyl |
| 36 | 2 | O | S | 1,5-Diphenyl-3-pentyl | 1,1-Dimethylpropyl |
| 37 | 2 | O | S | 1,5-Diphenyl-3-pentyl | Phenyl |
| 38 | 2 | O | S | 3-(4-Methoxyphenyl)propyl | 1,1-Dimethylpropyl |
| 39 | 2 | O | S | 3-(4-Methoxyphenyl)propyl | Phenyl |
| 40 | 2 | O | S | 3-(1-Naphthyl)propyl | 1,1-Dimethylpropyl |
| 41 | 1 | O | S | 3,3-Di(4-fluoro)phenyl-propyl | 1,1-Dimethylpropyl |
| 42 | 1 | O | S | 4,4-Di(4-fluoro)phenyl-butyl | 1,1-Dimethylpropyl |
| 43 | 1 | O | S | 3-(1-Naphthyl)propyl | 1,1-Dimethylpropyl |
| 44 | 1 | O | S | 2,2-Diphenylethyl | 1,1-Dimethylpropyl |
| 45 | 2 | O | S | 2,2-Diphenylethyl | 1,1-Dimethylpropyl |

TABLE I-continued

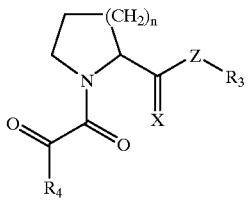

| No. | n | X | Z | R₃ | R₄ |
|---|---|---|---|---|---|
| 46 | 2 | O | S | 3,3-Diphenylpropyl | 1,1-Dimethylpropyl |
| 47 | 1 | O | S | 3-(4-{Trifluoromethyl}-phenyl)propyl | 1,1-Dimethylpropyl |
| 48 | 1 | O | S | 3-(2-Naphthyl)propyl | 1,1-Dimethylpropyl |
| 49 | 2 | O | S | 3-(1-Naphthyl)propyl | 1,1-Dimethylpropyl |
| 50 | 1 | O | S | 3-(3-Chloro)phenylpropyl | 1,1-Dimethylpropyl |
| 51 | 1 | O | S | 3-(3-{Trifluoromethyl}-phenyl)propyl | 1,1-Dimethylpropyl |
| 52 | 1 | O | S | 3-(2-Biphenyl)propyl | 1,1-Dimethylpropyl |
| 53 | 1 | O | S | 3-(2-Fluorophenyl)propyl | 1,1-Dimethylpropyl |
| 54 | 1 | O | S | 3-(3-Fluorophenyl)propyl | 1,1-Dimethylpropyl |
| 55 | 2 | O | S | 4-Phenylbutyl | 1,1-Dimethylpropyl |
| 56 | 2 | O | S | 3-Phenylpropyl | 1,1-Dimethylpropyl |
| 57 | 1 | O | S | 3-(2-Chloro)phenylpropyl | 1,1-Dimethylpropyl |
| 58 | 2 | O | S | 3-(3-Chloro)phenylpropyl | 1,1-Dimethylpropyl |
| 59 | 2 | O | S | 3-(2-Fluoro)phenylpropyl | 1,1-Dimethylpropyl |
| 60 | 2 | O | S | 3-(3-Fluoro)phenylpropyl | 1,1-Dimethylpropyl |
| 61 | 1 | O | S | 3-(3,4-Dimethoxyphenyl)-propyl | 1,1-Dimethylpropyl |
| 62 | 1 | O | CH₂ | 3-Phenylpropyl | Cyclohexyl |
| 63 | 1 | O | CH₂ | 2-Phenylethyl | tert-Butyl |
| 64 | 2 | O | CH₂ | 4-Phenylbutyl | Cyclohexyl |
| 65 | 2 | O | CHR₁ | 2-Phenylethyl | tert-Butyl |
| 66 | 1 | O | CH₂ | 3,3-Di(4-fluorophenyl)-propyl | 1,1-Dimethylpropyl |
| 67 | 2 | O | CH₂ | 3-Phenylpropyl | 1,1-Dimethylpropyl |
| 68 | 1 | O | CH₂ | 3-(4-Hydroxyphenyl)propyl | 1,1-Dimethylpropyl |
| 69 | 1 | O | bond | 3-Phenylpropyl | 1,1-Dimethylpropyl |
| 70 | 1 | O | bond | 3-(3-Pyridyl)propyl | tert-Butyl |
| 71 | 1 | O | bond | 3-(3-Pyridyl)propyl | Cyclohexyl |
| 72 | 2 | O | bond | 4-(4-Methoxyphenyl)butyl | 1,1-Dimethylpropyl |
| 73 | 2 | O | bond | 4-Phenylbutyl | 1,1-Dimethylpropyl |
| 74 | 2 | O | bond | 4-Phenylbutyl | Phenyl |

The most preferred examples of the compounds of TABLE I are named as follows:

1 (2S)-3,3-dimethyl-1-[2-(5-phenylpentanoyl)pyrrolidinyl]pentane-1,2-dione
2 (2S)-3,3-dimethyl-1-[2-(5-(3-pyridyl)pyrrolidinyl]pentane-1,2-dione
3 (2S)-2-({1-oxo-5-phenyl}-pentyl-1-(3,3-dimethyl-1,2-dioxobutyl)pyrrolidine
9 2-Phenyl-1-ethyl(2S)-1-(3,3-dimethyl-1,2-dioxopentyl)-2-pyrrolidinecarbothioate
10 2-Phenyl-1-ethyl 1-(3,3-dimethyl-1,2-dioxopentyl)-2-piperidinecarbothioate
11 1-{2-benzo[b]thiophen-3-ylmethylthio)carbonyl]pyrrolidinyl}-3,3-dimethylpentane-1,2-dione
12 2-Phenyl-1-ethyl(2S)-1-(2-cyclohexyl-1,2-dioxoethyl)-2-pyrrolidinecarbothioate
14 2-Phenyl-1-ethyl 1-(2-phenyl-1,2-dioxoethyl)-2-piperidinecarbothioate
17 2-({1-oxo-6-phenyl}-hexyl)(2S)-1-(3,3-dimethyl-1,2-dioxopentyl)piperidine
24 2-Phenyl-1-ethyl(2S)-1-(1-cyclopentyl-1,2-dioxoethyl)-2-pyrrolidinecarbothioate
25 3-Phenyl-1-propyl 1-(3,3-dimethyl-1,2-dioxobutyl)-2-piperidinecarbothioate
26 3-Phenyl-1-propyl(2S)-1-(3,3-dimethyl-1,2-dioxopentyl)-2-pyrrolidinecarbothioate
27 3-(3-Pyridyl)-1-propyl(2S)-1-(3,3-dimethyl-1,2-dioxopentyl)-2-pyrrolidinecarbothioate
28 3-Phenyl-1-propyl(2S)-1-(2-cyclohexyl-1,2-dioxoethyl)-2-pyrrolidinecarbothioate
29 4-Phenyl-1-butyl(2S)-1-(2-cyclohexyl-1,2-dioxoethyl)-2-pyrrolidinecarbothioate
30 4-Phenyl-1-butyl(2S)-1-(3,3-dimethyl-1,2-dioxopentyl)-2-pyrrolidinecarbothioate
31 3-(3-Pyridyl)-1-propyl(2S)-1-(2-cyclohexyl-1,2-dioxoethyl)-2-pyrrolidinecarbothioate
32 3,3-Diphenyl-1-propyl(2S)-1-(3,3-dimethyl-1,2-dioxopentyl)-2-pyrrolidinecarbothioate
33 3,3-Diphenyl-1-propyl(2S)-1-(2-cyclohexyl-1,2-dioxoethyl)-2-pyrrolidinecarbothioate
34 3-(para-Methoxyphenyl)-1-propyl(2S)-1-(3,3-di-methyl-1,2-dioxopentyl)-2-pyrrolidinecarbothioate
35 4-Phenyl-1-butyl 1-(1,2-dioxo-3,3-dimethylbutyl)-2-piperidinecarbothioate
36 1,5-Diphenyl-3-pentyl 1-(3,3-dimethyl-1,2-dioxopentyl)-2-piperidinecarbothioate
37 1,5-Diphenyl-3-pentyl 1-(2-phenyl-1,2-dioxoethyl)-2-piperidinecarbothioate
38 3-(para-Methoxyphenyl)-1-propyl 1-(1,2-dioxo-3,3-dimethylpentyl)piperidine-2-carbothioate
39 3-(para-Methoxyphenyl)-1-propyl 1-(2-phenyl-1,2-dioxoethyl)piperidine-2-carbothioate 40 3-(1-Naphthyl)-1-propyl 1-(3,3-dimethyl-1,2-dioxopentyl)piperidine-2-carbothioate
41 3,3-Di(para-fluoro)phenyl-1-propyl(2S)-1-(3,3-dimethyl-1,2-dioxopentyl)-2-pyrrolidinecarbothioate
42 4,4-Di(para-fluorophenyl)butyl 1-(3,3-dimethyl-2-oxopentanoyl)-2-pyrrolidinecarbothioate
43 3-(1-Naphthyl)-1-propyl(2S)-1-(3,3-dimethyl-2-oxopentanoyl)-2-pyrrolidinecarbothioate
44 2,2-Diphenylethyl(2S)-1-(3,3-dimethyl-2-oxopentanoyl)-2-pyrrolidinecarbothioate
45 2,2-Diphenylethyl(2S)-1-(3,3-dimethyl-2-oxopentanoyl)-2-piperidinecarbothioate
46 3,3-Diphenylpropyl 1-(3,3-dimethyl-2-oxopentanoyl)-2-piperidinecarbothioate
47 3-[4-(Trifluoromethyl)phenyl]propyl(2S)-1-(3,3-dimethyl-2-oxopentanoyl)-2-pyrrolidinecarbothioate
48 3-(2-Naphthyl)propyl(2S)-1-(3,3-dimethyl-2-oxopentanoyl)-2-pyrrolidinecarbothioate
49 3-(1-Naphthyl)-1-propyl 1-(3,3-dimethyl-2-oxopentanoyl)-2-piperidinecarbothioate
50 3-(3-Chlorophenyl)propyl(2S)-1-(3,3-dimethyl-2-oxopentanoyl)-2-pyrrolidinecarbothioate
51 3-[3-(Trifluoromethyl)phenyl]propyl(2S)-1-(3,3-dimethyl-2-oxopentanoyl)-2-pyrrolidinecarbothioate
52 3-(2-Biphenyl)propyl(2S)-1-(3,3-dimethyl-2-oxopentanoyl)-2-pyrrolidinecarbothioate
53 3-(2-Fluorophenyl)propyl(2S)-1-(3,3-dimethyl-2-oxopentanoyl)-2-pyrrolidinecarbothioate
54 3-(3-Fluorophenyl)propyl(2S)-1-(3,3-dimethyl-2-oxopentanoyl)-2-pyrrolidinecarbothioate
55 4-Phenylbutyl 1-(3,3-dimethyl-2-oxopentanoyl)-2-piperidinecarbothioate
56 3-Phenylpropyl 1-(3,3-dimethyl-2-oxopentanoyl)-2-piperidinecarbothioate
57 3-(2-Chlorophenyl)propyl(2S)-1-(3,3-dimethyl-2-oxopentanoyl)-2-pyrrolidinecarbothioate
58 3-(3-Chlorophenyl)-1-propyl 1-(3,3-dimethyl-2-oxopentanoyl)-2-piperidinecarbothioate
59 3-(2-Fluorophenyl)propyl 1-(3,3-dimethyl-2-oxopentanoyl)-2-piperidinecarbothioate
60 3-(3-Fluorophenyl)propyl 1-(3,3-dimethyl-2-oxopentanoyl)-2-piperidinecarbothioate
61 3-(3,4-Dimethoxyphenyl)propyl(2S)-1-(3,3-di-methyl-2-oxopentanoyl)-2-pyrrolidinecarbothioate
62 (2S)-2-({1-Oxo-5-phenyl}pentyl-1-(2-Cyclohexyl-1,2-dioxoethyl)pyrrolidine
63 2-(1-Oxo-4-phenyl)-butyl-1-(3,3-dimethyl-1,2-dioxobutyl)pyrrolidine
64 2-(1-Oxo-6-phenyl)-hexyl-1-(2-Cyclohexyl-1,2-dioxoethyl)piperidine
65 2-({1-Oxo-[2-{2'-phenyl}ethyl]-4-phenyl}-butyl-1-(3,3-dimethyl-1,2-dioxobutyl)piperidine
66 (2S)-2-[5,5-di(4-Fluorophenyl)pentanoyl]-1-(3,3 dimethyl-1,2-pentanedione)pyrrolidine
67 3,3-Dimethyl-1-[2-(5-phenylpentanoyl)piperidino]-1,2-pentanedione
68 (2S)-3,3-dimethyl-1-[2-(5-(4-hydroxyphenyl)pentanoyl) pyyrolidinyl]penatane-1,2-dione

FORMULA III

Another preferred embodiment is a compound of formula III:

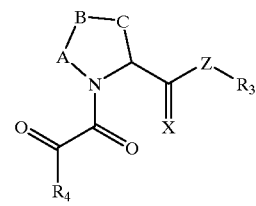

or a pharmaceutically acceptable salt, ester, or solvate thereof, wherein:

A, B, and C are independently $CH_2$, O, S, SO, $SO_2$, NH, or $NR_4$;

X is O or S;

Z is S, $CH_2$, $CHR_1$, or $CR_1R_2$;

$R_1$, $R_2$, and $R_3$ are independently $C_1$–$C_6$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_6$ straight or branched chain alkyl or alkenyl, $Ar_2$, or a combination thereof;

n is 1 or 2;

$R_4$ is either $C_1$–$C_9$ straight or branched chain alkyl or alkenyl, $C_3$–$C_8$ cycloalkyl, $C_5$–$C_7$ cycloalkenyl or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, hydroxyl, or a combination thereof; and $Ar_1$ and $Ar_2$ are independently a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino or a combination thereof; wherein the individual ring sizes are 5–6 members; and wherein the heterocyclic ring contains 1–6 heteroatom(s) selected from the group consisting of O, N, S, and a combination thereof.

Particularly preferred compounds of formula III are presented in TABLE II.

TABLE II

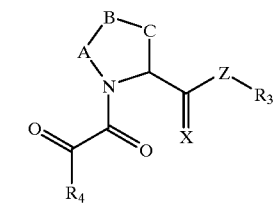

| No. | A | B | C | X | Z | $R_3$ | $R_4$ |
|---|---|---|---|---|---|---|---|
| 75 | $CH_2$ | S | $CH_2$ | O | S | 2-phenethyl | 1,1-Dimethyl-propyl |
| 76 | $CH_2$ | S | $CH_2$ | O | $CH_2$ | 3-phenylpropyl | 1,1-Dimethyl-propyl |
| 77 | $CH_2$ | $CH_2$ | NH | O | S | 2-phenethyl | 1,1-Dimethyl-propyl |

TABLE II-continued

| No. | A | B | C | X | Z | R₃ | R₄ |
|---|---|---|---|---|---|---|---|
| 78 | $CH_2$ | S | $CH_2$ | S | S | 2-phenethyl | 1,1-Dimethyl-propyl |

FORMULA IV

A further preferred embodiment of this invention is a compound of formula IV:

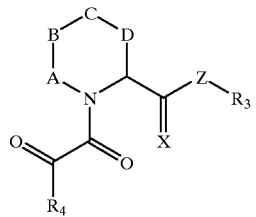

IV or a pharmaceutically acceptable salt, ester, or solvate thereof, wherein:

A, B, C, and D are independently $CH_2$, O, S, SO, $SO_2$, NH, or $NR_4$;

X is O or S;

Z is S, $CH_2$, $CHR_1$, or $CR_1R_2$;

$R_1$, $R_2$, and $R_3$ are independently $C_1$–$C_6$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_6$ straight or branched chain alkyl or alkenyl, $Ar_2$, or a combination thereof;

n is 1 or 2;

$R_4$ is either $C_1$–$C_9$ straight or branched chain alkyl or alkenyl, $C_3$–$C_8$ cycloalkyl, $C_5$–$C_7$ cycloalkenyl or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, hydroxyl, or a combination thereof; and $Ar_1$ and $Ar_2$ are independently a mono-, bi- or tricyclic, carbo- or heterocyclic ring, wherein the ring is either unsubstituted or substituted in one to three position(s) with halo, hydroxyl, nitro, trifluoromethyl, $C_{1-6}$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; and wherein the heterocyclic ring contains 1–6 heteroatom(s) selected from the group consisting of O, N, S, and a combination thereof.

Particularly preferred compounds of formula IV are presented in TABLE III.

TABLE III

| No. | A | B | C | D | X | Z | R₃ | R₄ |
|---|---|---|---|---|---|---|---|---|
| 79 | $CH_2$ | $CH_2$ | O | $CH_2$ | O | $CH_2$ | 3-phenyl-propyl | 1,1-Dimethyl-propyl |
| 80 | $CH_2$ | $CH_2$ | O | $CH_2$ | O | S | 2-phenethyl | 1,1-Dimethyl-propyl |
| 81 | $CH_2$ | $CH_2$ | S | $CH_2$ | O | $CH_2$ | 3-phenyl-propyl | 1,1-Dimethyl-propyl |
| 82 | $CH_2$ | $CH_2$ | S | $CH_2$ | O | S | 2-phenethyl | 1,1-Dimethyl-propyl |

The compounds of this invention possess at least one asymmetric center and thus can be produced as mixtures of stereoisomers or as individual R- and S-stereoisomers. The individual enantiomers may be obtained by using an optically active starting material, by resolving a racemic or non-racemic mixture of an intermediate at some appropriate stage of the synthesis, or by resolving a compound of the present invention. It is understood that the individual R- and S-stereoisomers as well as mixtures (racemic and non-racemic) of stereoisomers are encompassed by this invention. The S-stereoisomer is most preferred.

Synthesis of Pyrrolidine Derivatives

The compounds of formulas I to IV may be prepared by a variety of synthetic sequences that utilize established chemical transformations. The general pathway to the present compounds is described in Scheme I. Starting compounds may be reacted with a variety of alkenyl magnesium halides to form olefin intermediates (1), which are in turn reacted sequentially with trifluroacetic acid, then methyl oxalyl chloride and triethylamine. The resulting oxamates (2) may be reacted with a variety of carbon nucleophiles, such as $R_1$—MgCl, to obtain further olefin intermediates (3). These intermediates are then reacted with a variety of organohalogen compounds, such as $R_2$—Br, to produce product (4), which is hydrogenated to produce compounds of the present invention (5).

SCHEME I

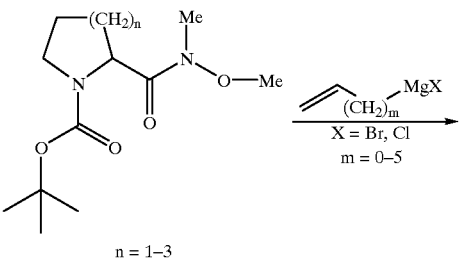

n = 1–3

-continued

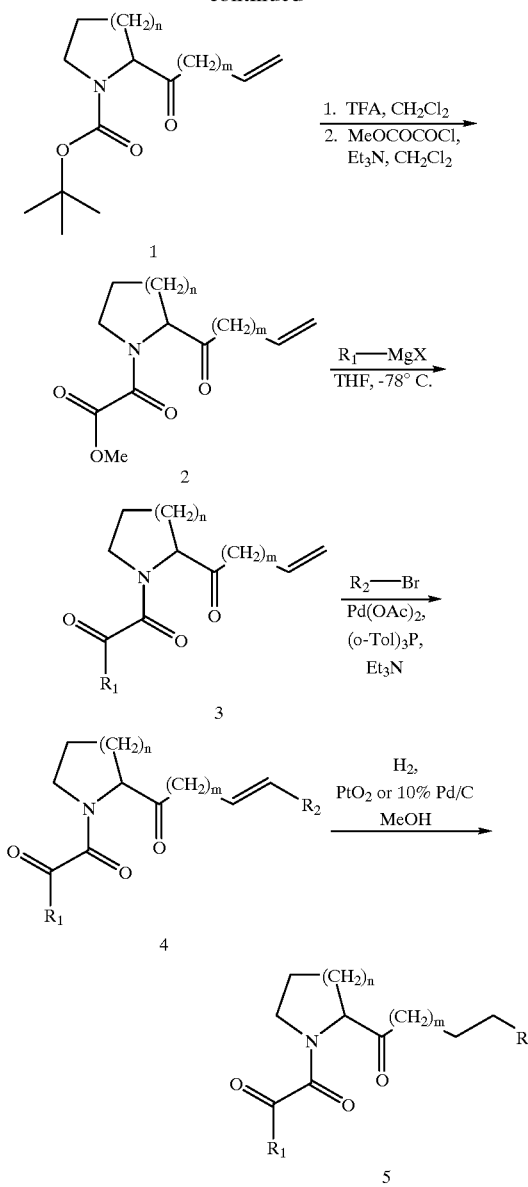

Methods of Using the Compounds of the Invention

The present invention further relates to the use of a compound of the present invention in the preparation of a medicament for effecting a neuronal activity in an animal.

Further, the present invention relates to a method of effecting a neuronal activity in an animal, comprising administering to said animal a neurotrophically effective amount of a compound of the present invention.

As neurotrophic agents, the compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertebrate disk syndromes, cervical spondylosis, plexus disorders, thoracic outlet destruction syndromes, peripheral neuropathies such as those caused by lead, dapsone, ticks, prophyria, Gullain-Barré syndrome, Alzheimer's disease, Huntington's Disease, or Parkinson's disease.

For these purposes, the compounds may be administered orally, parenterally, by inhalation spray, topically, rectally, nasally, buccally, vaginally, or via an implanted reservoir in dosage formulations containing conventional non-toxic pharmaceutically-acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques.

To be effective therapeutically as central nervous system targets, the compounds should readily penetrate the blood-brain barrier when peripherally administered. Compounds which cannot penetrate the blood-brain barrier can be effectively administered by an intraventricular route.

The compounds may be administered in the form of sterile injectable preparations, for example, as sterile injectable aqueous or oleaginous suspensions. These suspensions, may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, the compounds may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax, and polyethylene glycols.

Furthermore, the compounds may be administered topically, especially when the conditions addressed for treatment involve areas or organs readily accessible by topical application, including neurological disorders of the eye, the skin, or the lower intestinal tract. Suitable topical formulations can be readily prepared for each of these areas.

For topical application to the eye, or ophthalmic use, the compounds can be formulated as micronized suspensions in isotonic, pH adjusted sterile saline, or, preferably, as a solution in isotonic, pH adjusted sterile saline, either with or without a preservative such as benzylalkonium chloride. Alternatively, the compounds may be formulated into ointments, such as petrolatum, for ophthalmic use.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax, and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol, and water.

Topical application to the lower intestinal tract can be effected in a rectal suppository formulations (see above) or in suitable enema formulations.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disease being treated; and the form of administration.

As neurotrophic agents, the compounds can be administered with other neurotrophic agents such as neurotrophic growth factor, brain derived growth factor, glial derived growth factor, cilial neurotrophic factor, insulin growth factor and active truncated derivatives thereof, acidic fibroblast growth factor, basic fibroblast growth factor, platelet-derived growth factors, neurotropin-3, and neurotropin 4/5. The dosage level of other neurotrophic drugs will depend upon the factors previously stated and the neurotrophic effectiveness of the drug combination.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

Pharmaceutical Compositions of the Invention

The present invention also relates to a pharmaceutical composition comprising:

(i) an effective amount of a compound of the present invention; and (ii) a pharmaceutically acceptable carrier.

In a preferred embodiment, such pharmaceutical composition is effective for effecting a neuronal activity, for treating neurodegenerative diseases, neurological disorders, and nerve damage, or for promoting nerve growth in an animal.

The above discussion relating to the utility and administration of the compounds of the present invention also applies to the pharmaceutical compositions of the present invention.

EXAMPLES

The following examples are illustrative of the present invention and are not intended to be limitations thereon. Unless otherwise specified, all percentages are based on 100% by weight of the final compound.

Example 1

Synthesis of (2S)-2-({1-oxo-5-phenyl}-pentyl-1-(3, 3-dimethyl-1,2-dioxopentyl)pyrrolidine (1)

(2S)-2-(1-oxo-5-phenyl)pentyl-N-benzylpyrrolidine. 1-chloro-4-phenylbutane (1.78 g; 10.5 mmol) in 20 mL of THF was added to 0.24 g (10 mmol) of magnesium turnings in 50 mL of refluxing THF. After the addition was complete, the mixture was refluxed for an additional 5 hours, and then added slowly to a refluxing solution of N-benzyl-L-proline ethyl ester (2.30 g (10 mmol) in 100 mL of THF. After 2 hours of further reflux, the mixture was cooled and treated with 5 mL of 2 N HCl. The reaction mixture was diluted with ether (100 mL) and washed with saturated $NaHCO_3$, water and brine. The organic phase was dried, concentrated and chromatographed, eluting with 5:1 $CH_2Cl_2$:EtOAc to obtain 2.05 g (64%) of the ketone as an oil, $^1H$ NMR ($CDCl_3$; 300 MHz): 1.49–2.18 (m, 8H); 2.32–2.46 (m, 1H); 2.56–2.65 (m, 2H); 2.97–3.06 (m, 1H); 3.17–3.34 (m, 1H); 3.44–3.62 (m, 1H); 4.02–4.23 (m, 2H); 7.01–7.44 (m, 10H).

(2S)-2-(1-oxo-5-phenyl)pentylpyrrolidine. The ketone compound (500 mg) and palladium hydroxide (20% on carbon, 50 mg) was hydrogenated at 40 psi in a Paar shaker overnight. The catalyst was removed by filtration and the solvent was removed in vacuo. The free amine was obtained as a yellow oil (230 mg; 100%), $^1H$ NMR ($CDCl_3$; 300 MHz): 1.75–2.34 (m, 10H); 2.55 (m, 2H); 2.95 (dm, 1H); 3.45–3.95 (m, 1H); 4.05 (m, 1H); 7.37 (m, 5H).

(2S)-2-(1-oxo-5-phenyl)pentyl-1-(1,2-dioxo-2-methoxyethyl)pyrrolidine. To a solution of (2S)-2-(1-oxo-4-phenyl)butylpyrrolidine (230 mg; 1.0 mmol) in $CH_2Cl_2$ (20 mL) at 0° C. was added dropwise methyloxalyl chloride (135 mg; 1.1 mmol). After stirring at 0° C. for 3 hours, the reaction was quenched with saturated $NH_4Cl$ and the organic phase was washed with water and brine and dried and concentrated. The crude residue was purified on a silica gel column, eluting with 20:1 $CH_2Cl_2$:EtOAc to obtain 300 mg of the oxamate as a clear oil (98%), $^1H$ NMR ($CDCl_3$; 300 MHz): 1.68 (m, 4H); 1.91–2.38 (m, 4H); 2.64 (t, 2H); 3.66–3.80 (m, 2H); 3.77, 3.85 (s, 3H total); 4.16 (m, 2H); 4.90 (m, 1H); 7.16 (m, 3H); 7.27 (m, 2H).

(2S)-2-({1-oxo-5-phenyl}-pentyl-1-(3,3-dimethyl-1,2-dioxopentyl)pyrrolidine (1). To a solution of the oxamate above (250 mg; 0.79 mmol) in anhydrous ether (15 mL), cooled to −78° C., was added 1,1-dimethylpropyl-magnesium chloride (0.8 mL of a 1.0 M solution in ether; 0.8 mmol). After stirring the resulting mixture at −78° C. for 2 hours, the reaction was quenched by the addition of 2 mL of saturated $NH_4Cl$, followed by 100 mL of EtOAc. The organic phase was washed with brine, dried, concentrated, and purified on a silica gel column, eluting with 50:1 $CH_2Cl_2$:EtOAc. Compound 1 was obtained as a clear oil, 120 mg, $^1$H NMR ($CDCl_3$, 300 MHz): δ 0.87 (t, 3H, J=7.5); 1.22 (s, 3H); 1.25 (s, 3H); 1.67 (m, 4H); 1.70–2.33 (m, 6H); 2.61 (t, 2H, J=7.1); 3.52 (m, 2H); 4.17 (t, 2H, J=6.2); 4.52 (m, 1H); 7.16–7.49 (m, 5H). Anal. Calcd. for $C_{22}H_{31}NO_3$—$H_2O$: C, 70.37; H, 8.86; N, 3.73. Found: 70.48; H, 8.35; N, 3.69.

Example 2

Synthesis of 2-({1-oxo-6-phenyl}hexyl)(2S)-1-(3,3-dimethyl-1,2-dioxopentyl)piperidine (17)

The method of Example 1 was utilized to prepare 2-({1-oxo-6-phenyl}hexyl)(2S)-1-(3,3-dimethyl-1,2-dioxopentyl) piperidine (17), utilizing 2-(ethoxy carboxylate)N-benzylpiperidine and 1-chloro-5-phenyl pentane as the starting materials.

Example 3

Synthesis of 2-(1-Oxo-4-phenyl)butyl-1-(3,3-dimethyl-1,2-dioxobutyl)pyrrolidine (63)

The method of Example 1 was utilized to prepare 2-(1-Oxo-4-phenyl)butyl-1-(3,3-dimethyl-1,2-dioxobutyl) pyrrolidine (63), utilizing 1-chloro-4-(4-hydroxyphenyl) butane, for 1-chloro-4-phenylbutane, as a starting material.

Example 4

Synthesis of (2S)-3,3-dimethyl-1-[2-(5-(3-pyridyl) pyrrolidinyl]pentane-1,2-dione (2)

Tert-butyl 2-pent-4-enoylpyrrolidinecarboxylate. To a solution of 3-butenylmagnesiumbromide (97 ml of a 0.5 M solution; 48.4 mmol) in THF (15 ml), cooled to 0° C. and under a nitrogen atmosphere, was added dropwise with stirring a solution of tert-butyl 2-(N-methoxy-N-methylcarbamoyl)pyrrolidine carboxylate (5.0 g, 19.4 mmol) in 15 ml of THF. The mixture was stirred overnight while slowly coming to room temperature. The reaction was quenched by the addition of 80 ml saturated $NH_4Cl$ followed by 50 ml of ethyl acetate and 20 ml of water. The layers were separated, and the aqueous layer was extracted with 2×100 ml ethyl acetate. The combined organic layers were dried over $MgSO_4$, filtered, concentrated, and the crude product was purified on a silica gel column with 10% ethyl acetate in hexane to obtain the olefin tert-butyl 2-pent-4-enoylpyrrolidine carboxylate as a clear oil, 4.30 g (88%): $^1$H NMR ($CDCl_3$, 400 MHz): d.

Methyl 2-oxo-2-(2-pent-4-enoylpyrrolidinyl)acetate. Trifluoroacetic acid ("TFA"; 65.7 g; 576 mmol) was added dropwise to a solution of 24.3 g (96 mmol) of tert-butyl (2-pent-4-enoyl)pyrrolidinecarboxylate in 45 ml of $CH_2Cl_2$, cooled to 0° C. After stirring for 4 hours, Thin Layer Chromatography ("TLC") indicated that the reaction was complete, and the mixture was concentrated in vacuo to remove TFA. The residue was dissolved in 800 ml of $CH_2Cl_2$ and treated with 2 equivalents of triethylamine while stirring and cooling the mixture in an ice bath. Methyl oxalyl chloride (13.5 g; 106 mmol) was added as a solution in 40 ml $CH_2Cl_2$, in 10 ml portions each followed by 5 ml of $Et_3N$. After the addition, a final 10 ml portion of $Et_3N$ was added and the mixture was stirred overnight. It was concentrated, treated with 100 ml of 1:1 ethyl acetate/hexane), filtered to remove solids, and the concentrated residue purified by SGC, eluting with 1:1 hexane/ethyl acetate, to obtain the oxamate methyl 2-oxo-2-(2-pent-4-enoylpyrrolidinyl)acetate as a brownish oil, 18.80 g (82%). $^1$H NMR ($CDCl_3$, 400 MHz): d.

3,3-Dimethyl-1-(2-pent-4-enoylpyrrolidinyl)pentane-1,2-dione. A solution of methyl 2-oxo-2-(2-pent-4-enoylpyrrolidinyl)acetate (21.0 g; 88 mmol) in 150 ml THF was cooled to −78° C., under nitrogen, and treated with 200 ml (180 mmol) of 0.9 M 3,3-dimethylpropyl magnesium chloride. After stirring for 2.5 hours, TLC indicated that the reaction was complete. It was quenched with 300 ml of saturated $NH_4Cl$ followed by 200 ml of ethyl acetate. The layers were separated and the aqueous layer was extracted once more with 300 ml of ethyl acetate. The combined organic layers were dried over $MgSO_4$, filtered, concentrated, and the product purified on silica gel with 20% ethyl acetate in hexane, to obtain 3,3-dimethyl-1-(2-pent-4-enoylpyrrolidinyl)pentane-1,2-dione as a light yellow oil, 21.0 g (85%).

3,3-Dimethyl-1-[2-(5-(3-pyridyl)pent-4-enoyl) pyrrolidinyl]pentane-1,2-dione. To a solution of olefin 3,3-dimethyl-1-(2-pent-4-enoylpyrrolidinyl)pentane-1,2-dione (500 mg; 1.78 mmol) in 7 ml of $Et_3N$ was added 3-bromopyridine (310 mg; 1.96 mmol), palladium (II) acetate (20 mg; 0.09 mmol), and tri-(orthotolyl)phosphine (108 mg; 0.36 mmol), and the mixture was refluxed overnight. The mixture was concentrated and the products purified on a silica gel column, eluting with a gradient from 50% ethyl acetate in hexane to 75% ethyl acetate. Two products were obtained as light yellow oils. The major product (85% of the mixture) was the product of aryl coupling to the terminus of the C—C double bond, 3,3-dimethyl-1-[2-(5-(3-pyridyl)pent-4-enoyl)pyrrolidinyl]pentane-1,2-dione; the minor product was the product of coupling at the more substituted carbon. The overall yield of the desired product was 480 mg (75%).

3,3-Dimethyl-1-[2-(5-(3-pyridyl)pentanoyl)pyrrolidinyl] pentane-1,2-dione (2). Platinum oxide (12 mg) was added to a solution of 3,3-dimethyl-1-[2-(5-(3-pyridyl)pent-4-enoyl) pyrrolidinyl]pentane-1,2-dione (300 mg; 0.84 mmol) in methanol (8 ml). The mixture was hydrogenated at 1 atm. for 2.5 hours. TLC indicated that the reaction was complete, and it was filtered through Celite and concentrated. Eluting through a plug of silica gel (ethyl acetate) furnished analytically pure material, 260 mg (87%). $^1$H NMR ($CDCl_3$, 400 MHz): δ0.87 (t, 3H, J=7.5); 1.21 (s, 6H); 1.64 (m, 4H); 1.69 (m, 2H); 1.78 (m, 1H); 1.96 (m, 2H); 2.15 (m, 1H); 2.53 (m, 1H); 2.63 (m, 2H); 3.49 (m, 1H); 3.53 (m, 1H); 4.57 (dd, 1H, J=8.8, 4.8); 7.20 (m, 1H); 7.49 (m, 1H, J=7.8); 8.44 (m, 2H). Anal. Calcd. for $C_{21}H_{30}N_2O_3$: C, 70.36; H, 8.44; N, 7.81. Found: C, 70.15; H, 8.54; N, 7.76. TLC: $R_1$=0.80 (ethyl acetate:ethanol 4:1). Note: this final hydrogenation step may be done using 10% Pd/C, and hydrogenating for 5 hours at 60 psi. Ethanol or ethyl acetate may be used instead of methanol.

Example 5

Synthesis of (2S)-3,3-dimethyl-1-[2-(5-(4-hydroxyphenyl)pentanoyl)pyyrolidinyl]pentane-1,2-dione (68)

The method of Example 4 was utilized to prepare 3,3-dimethyl-1-(2-pent-4-enoylpyrrolidinyl)pentane-1,2-dione.

3,3-Dimethyl-1-(2-{5-[4-(phenylmethoxy)phenyl]pent-4-enoyl}pyrrolidinyl)pentane-1,2-dione. A solution of 3,3-dimethyl-1-(2-pent-4-enoylpyrrolidinyl)pentane-1,2-dione (1.73 g; 6.20 mmol), 4-benzyloxybromobenzene (1.80 g;

6.83 mmol), palladium (II) acetate (70 mg; 0.31 mmol), and tri(orthotolyl)phosphine (380 mg; 1.24 mmol) in triethylamine (23 ml) was refluxed overnight. The mixture was concentrated in vacuo and purified on a silica gel column, eluting with a gradient from 10% ethyl acetate/hexane to 20% ethyl acetate/hexane, to obtain 1.72 g (60%) of 3,3-dimethyl-1-(2-{5-[4-(phenylmethoxy)phenyl]pent-4-enoyl}pyrrolidinyl)pentane-1,2-dione as a yellow oil.

1-{2-[5-(4-Hydroxyphenyl)pentanoyl]pyrrolidinyl}-3,3-dimethylpentane-1,2-dione (68). A mixture of 1.63 g (3.53 mmol) of 3,3-dimethyl-1-(2-{5-[4-(phenylmethoxy)phenyl]pent-4-enoyl}pyrrolidinyl)pentane-1,2-dione and 400 mg of 10% Pd/C in 100 ml of ethyl acetate was hydrogenated at 50 psi overnight. The mixture was filtered through Celite, concentrated, and chromatographed (25% ethyl acetate/hexane) to obtain 800 mg (61%) of 1-{2-[5-(4-hydroxyphenyl)pentanoyl]pyrrolidinyl}-3,3-dimethylpentane-1,2-dione (68). $^1$H NMR (CDCl$_3$, 400 MHz): δ0.87 (t, 3H, J=7.50); 1.21 (s, 6H); 1.63 (m, 4H); 1.67 (m, 2H); 1.93 (m, 3H); 2.04 (m, 1H); 2.52 (m, 4H); 3.47 (m, 2H); 4.57 (m, 1H); 6.72 (d, 2H, J=8.40); 7.03 (d, 2H, J=8.40). Anal. Calcd. for C$_{22}$H$_{31}$NO$_4$: C, 70.75; H, 8.37; N, 3.75. Found: C, 70.64; H, 8.44; N, 3.65. TLC: R$_f$=0.45 (25% ethyl acetate/hexane).

Example 6

Synthesis of 2-phenyl-1-ethyl 1-(3,3-dimethyl-1,2-dioxopentyl)-2-piperidinecarbothioate (10)

Methyl(2S)-1-(1,2-dioxo-2-methoxyethyl)-2-pyrrolidinecarboxylate. A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 ml) was added dropwise. The resulting mixture was stirred at 0° C. for 1.5 hour. After filtering to remove solids, the organic phase was washed with water, dried over MgSO$_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR (CDCl$_3$): δ1.93 (dm, 2H); 2.17(m, 2H); 3.62(m, 2H); 3.71 (s, 3H); 3.79, 3.84 (s, 3H total); 4.86 (dd, 1H, J=8.4, 3.3).

Methyl(2S)-1-(1,2-dioxo-3,3-dimethylpentyl)-2-pyrrolidinecarboxylate. A solution of methyl(2S)-1-(1,2-dioxo-2-methoxyethyl)-2-pyrrolidinecarboxylate (2.35 g; 10.90 mmol) in 30 ml of tetrahydrofuran (THF) was cooled to −78° C. and treated with 14.2 ml of a 1.0 M solution of 1,1-dimethylpropylmagnesium chloride in THF. After stirring the resulting homogeneous mixture at −78° C. for three hours, the mixture was poured into saturated ammonium chloride (100 ml) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil, $^1$H NMR (CDCl$_3$): δ0.88 (t, 3H); 1.22, 1.26 (s, 3H each); 1.75(dm, 2H); 1.87–2.10 (m, 3H); 2.23 (m, 1H); 3.54 (m, 2H); 3.76 (s, 3H); 4.52 (dm, 1H, J=8.4, 3.4).

(2S)-1-(1,2-dioxo-3,3-dimethylpentyl)-2-pyrrolidinecarboxylic acid. A mixture of methyl(2S)-1-(1,2-dioxo-3,3-dimethylpentyl)-2-pyrrolidinecarboxylate (2.10 g; 8.23 mmol), 1 N LiOH (15 ml), and methanol (50 ml) was stirred at 0° C. for 30 minutes and at room temperature overnight. The mixture was acidified to pH 1 with 1 N HCl, diluted with water, and extracted into 100 ml of methylene chloride. The organic extract was washed with brine and concentrated to deliver 1.73 g (87%) of snow-white solid which did not require further purification, $^1$H NMR (CDCl$_3$): δ0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

2-phenyl-1-ethyl 1-(3,3-dimethyl-1,2-dioxopentyl)-2-piperidinecarbothioate (10). To a solution of (2S)-1-(1,2-dioxo-3,3-dimethylpentyl)-2-pyrrolidinecarboxylic acid (241 mg; 1.0 mmol) in CH$_2$Cl$_2$ (10 ml) was added dicyclohexylcarbodiimide (226 mg; 1.1 mmol). After stirring the resulting mixture for 5 minutes, the solution was cooled to 0° C. and treated with a solution of phenyl mercaptan (138 mg; 1.0 mmol) and 4-dimethylaminopyridine (6 mg) in 5 ml of CH$_2$Cl$_2$. The mixture was allowed to warm to room temperature with stirring overnight. The solids were removed by filtration and the filtrate was concentrated in vacuo; the crude residue was purified by flash chromatography (10:1 hexane:EtOAc) to obtain 302 mg (84%) of 10 as an oil, $^1$H NMR (CDCl$_3$, 300 MHZ): δ0.85 (t, 3H, J=$_{7.5}$); 1.29 (s, 3H); 1.31 (s, 3H); 1.70–2.32 (m, 6H); 2.92 (t, 2H, J=7.4); 3.22(t, 2H, J=7.4); 3.58 (m, 2H); 4.72 (m, 1H); 7.23–7.34 (m, 5H). Anal. Calcd. for C$_{20}$H$_{27}$NO$_3$S·0.4H$_2$O: C, 65.15; H, 7.60; N, 3.80. Found: C, 65.41; H, 7.49; N, 3.72.

Example 7

Synthesis of 2-phenyl-1-ethyl(2S)-1-(3,3-dimethyl-1,2-dioxopentyl)-2-pyrrolidinecarbothioate (9)

Methyl 1-(1,2-dioxo-2-methoxyethyl)-2-piperidinecarboxylate. A solution of methyl pipecolate hydrochloride (8.50 g; 47.31 mmol) in dry methylene chloride (100 ml) was cooled to 0° C. and treated with triethylamine (10.5 g; 103 mmol; 2.1 eq). After stirring the formed slurry under a nitrogen atmosphere for 15 minutes, a solution of methyl oxalyl chloride (8.50 g; 69.4 mmol) in methylene chloride (75 ml) was added dropwise. The resulting mixture was stirred at 0° C. for 1.5 hours. After filtering to remove solids, the organic phase was washed with water, dried over MgSO$_4$ and concentrated. The crude residue was purified on a silica gel column, eluting with 50% ethyl acetate in hexane, to obtain 9.34 g (86%) of the product as a reddish oil. Mixture of cis-trans amide rotamers; data for trans rotamer given. $^1$H NMR (CDCl$_3$): δ1.22–1.45 (m, 2H); 1.67–1.78 (m, 3H); 2.29 (m, 1H); 3.33 (m, 1H); 3.55 (m, 1H); 3.76 (s, 3H); 3.85, 3.87 (s, 3H total); 4.52 (dd, 1H).

Methyl 1-(1,2-dioxo-3,3-dimethylpentyl)-2-piperidinecarboxylate. A solution of methyl 1-(1,2-dioxo-2-methoxyethyl)-2-piperidinecarboxylate (3.80 g; 16.57 mmol) in 75 ml of tetrahydrofuran (THF) was cooled to −78° C. and treated with 20.7 ml of a 1.0 M solution of 1,1-dimethyl-propylmagnesium chloride in THF. After stirring the resulting homogeneous mixture at −78° C. for three hours, the mixture was poured into saturated ammonium chloride (100 ml) and extracted into ethyl acetate. The organic phase was washed with water, dried, and concentrated, and the crude material obtained upon removal of the solvent was purified on a silica gel column, eluting with 25% ethyl acetate in hexane, to obtain 3.32 g (74%) of the oxamate as a colorless oil, $^1$H NMR (CDCl$_3$): δ0.88 (t, 3H); 1.21, 1.25 (s, 3H each); 1.35–1.80 (m, 7H); 2.35 (m, 1H); 3.24 (m, 1H); 3.41 (m, 1H); 3.76 (s, 3H); 5.32 (d, 1H).

1-(1,2-dioxo-3,3-dimethylpentyl)-2-piperidinecarboxylic acid. A mixture of methyl 1-(1,2-dioxo-3,3-dimethylpentyl)-2-piperidinecarboxylate (3.30 g; 12.25 mmol), 1 N LiOH (15 ml), and methanol (60 ml) was stirred at 0° C. for 30 minutes and at room temperature overnight. The mixture was acidified to pH 1 with 1 N HCl, diluted with water, and extracted into 100 ml of methylene chloride. The organic extract was washed with brine and concentrated to deliver 2.80 g (87%) of snow-white solid which did not require further purification, $^1$H NMR (CDCl$_3$): δ0.89 (t, 3H); 1.21, 1.24 (s, 3H each); 1.42–1.85 (m, 7H); 2.35 (m, 1H); 3.22 (d, 1H); 3.42(m, 1H); 5.31 (d, 1H).

2-phenyl-1-ethyl(2S)-1-(3,3-dimethyl-1,2-dioxopentyl)-2-pyrrolidinecarbothioate (9). To a solution of 1-(1,2-dioxo-3,3-dimethylpentyl)-2-piperidine-carboxylic acid (255 mg; 1.0 mmol) in CH$_2$Cl$_2$ (10 ml) was added dicyclohexylcarbodiimide (226 mg; 1.1 mmol). After stirring the resulting mixture for 5 minutes, the solution was cooled to 0° C. and treated with a solution of phenyl mercaptan (138 mg; 1.0 mmol) and 4-dimethylaminopyridine (6 mg) in 5 ml of CH$_2$Cl$_2$. The mixture was allowed to warm to room temperature with stirring overnight. The solids were removed by filtration and the filtrate was concentrated in vacuo; the crude residue was purified by flash chromatography (10:1 hexane:EtOAc) to obtain 300 mg (80%) of 9 as an oil, $^1$H NMR (CDCl$_3$, 300 MHZ): d 0.94 (t, 3H, J=7.5); 1.27 (s, 3H); 1.30 (s, 3H); 1.34–1.88 (m, 7H); 2.45 (m, 1H); 2.90 (t, 2H, J=$_{7,7}$); 3.26 (t, 2H, J=7.7); 3.27 (m, 1H); 3.38 (m, 1H); 5.34 (m, 1H); 7.24–7.36 (m, 5H). Anal. Calcd. for C$_{21}$H$_{29}$NO$_3$S: C, 67.17; H, 7.78; N, 3.73. Found: C, 67.02; H, 7.83; N, 3.78.

Example 8

A patient is suffering from a condition or disorder requiring stimulation of damaged neurons, promotion of neuronal regeneration, prevention of neurodegeneration, or treatment of a neurological disorder; wherein the neurological disorder is selected from the group consisting of peripheral neuropathy caused by physical injury or disease state, traumatic injury to the brain, physical damage to the spinal cord, stroke associated with brain damage, and neurological disorders relating to neurodegeneration; and wherein the neurological disorder relating to neurodegeneration is selected from the group consisting of Alzheimer's Disease, Huntington's Disease, Parkinson's Disease, and amyotrophic lateral sclerosis. (2S3)-3,3-dimethyl-1-[2-(5-(3-pyridyl)pyrrolidinyl] pentane-1,2-dione, 2-(1-Oxo-4-phenyl)-butyl-1-(3,3-dimethyl-1,2-dioxobutyl)pyrrolidine, (2S)-3,3-dimethyl-1-[2-(5-(4-hydroxyphenyl)pentanoyl)pyrrolidinyl]pentane-1,2-dione, or 2-({1-oxo-6-phenyl}-hexyl)(2S)-1-(3,3-dimethyl-1,2-dioxopentyl)piperidine, or a pharmaceutical composition comprising the same, may be administered to the patient. Protection from or recovery from the effects of the described condition(s) or disorders is expected to occur following treatment.

The compounds of the present invention have an affinity for the FK506 binding protein, particularly FKBP12. The inhibition of the prolyl peptidyl cis-trans isomerase activity of FKBP may be measured as an indicator of this affinity and as a possible indicator of neurotrophic activity.

K$_i$ Test Procedure

Inhibition of the peptidyl-prolyl isomerase (rotamase) activity of the inventive compounds can be evaluated by known methods described in the literature (Harding et al., Nature, 1989, 341:758–760; Holt et al. J. Am. Chem. Soc., 115:9923–9938). These values are obtained as apparent K$_i$'S, and are presented for representative compounds in Table IV. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent K$_i$ values.

In a plastic cuvette are added 950 ml of ice cold assay buffer (25 mM HEPES, pH 7.8, 100 mM NaCl), 10 ml of FKBP (2.5 mM in 10 mM Tris-Cl pH 7.5, 100 mM NaCl, 1 mM dithiothreitol), 25 ml of chymotrypsin (50 mg/ml in 1 mM HCl) and 10 ml of test compound at various concentrations in dimethyl sulfoxide. The reaction is initiated by the addition of 5 ml of substrate (succinyl-Ala-Phe-Pro-Phe-para-nitroanilide, 5 mg/ml in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table IV under the column "Ki".

The neurotrophic effects of the compounds of the present invention can be demonstrated in cellular biological experiments in vitro, as described below.

Chick Dorsal Root Ganglion Cultures and Neurite Outgrowth

The neurotrophic effects of the FKBP inhibitor compounds were demonstrated by evaluating the ability of the compounds to promote neurite outgrowth in cultured chick sensory neurons from dorsal root ganglia. Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 μM cytosine β-D arabinofuranoside (Ara C) at 37° C. in an environment containing 5% CO$_2$. Twenty-four hours later, the DRGs were treated with various concentrations of nerve growth factor, immunophilin ligands or combinations of NFG plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

Dose-response curves were generated from which ED$_{50}$ values were obtained. The results of these experiments are presented in Table IV under the column "ED50". Representative photomicrographs of untreated (control) sensory neurons and of sensory neurons treated with compound 1 (10 pM, 1 nM, 1 μM), and related compounds 2-Phenyl-1-ethyl (2S)-1-(3,3-dimethyl-1,2-dioxopentyl)-2-pyrrolidinecarbothioate (10 pM, 1 nM, 100 nM) and 2-Phenyl-1-ethyl 1-(3,3-dimethyl-1,2-dioxopentyl)-2-piperidinecarbothioate (10 pM, 1 nM, 100 nM) promoting neurite outgrowth in sensory neurons are shown in FIGS. 1(A–D), 2(A–D), and 3(A–D), respectively.

MPTP Model of Parkinson's Disease

The remarkable neurotrophic and neuroregenerative effects of the present inventive compounds were further demonstrated in an animal model of neurodegenerative disease. MPTP lesioning of dopaminergic neurons in mice was used as an animal model of Parkinson's Disease. Four week old male CD1 white mice were dosed i.p. with 30 mg/kg of MPTP for 5 days. Test compounds (4 mg/kg), or vehicle, were administered s.c. along with the MPTP for 5 days, as well as for an additional 5 days following cessation of MPTP treatment. At 18 days following MPTP treatment, the animals were sacrificed and the striata were dissected and homogenized. Immunostaining was performed on saggital and coronal brain sections using anti-tyrosine hydroxylase 1 g to quantitate survival and recovery of dopaminergic neurons. In animals treated with MPTP and vehicle, a substantial loss of functional dopaminergic terminals was observed as compared to non-lesioned animals. Lesioned animals receiving test compounds showed a significant recovery of TH-stained dopaminergic neurons.

Figure 4:
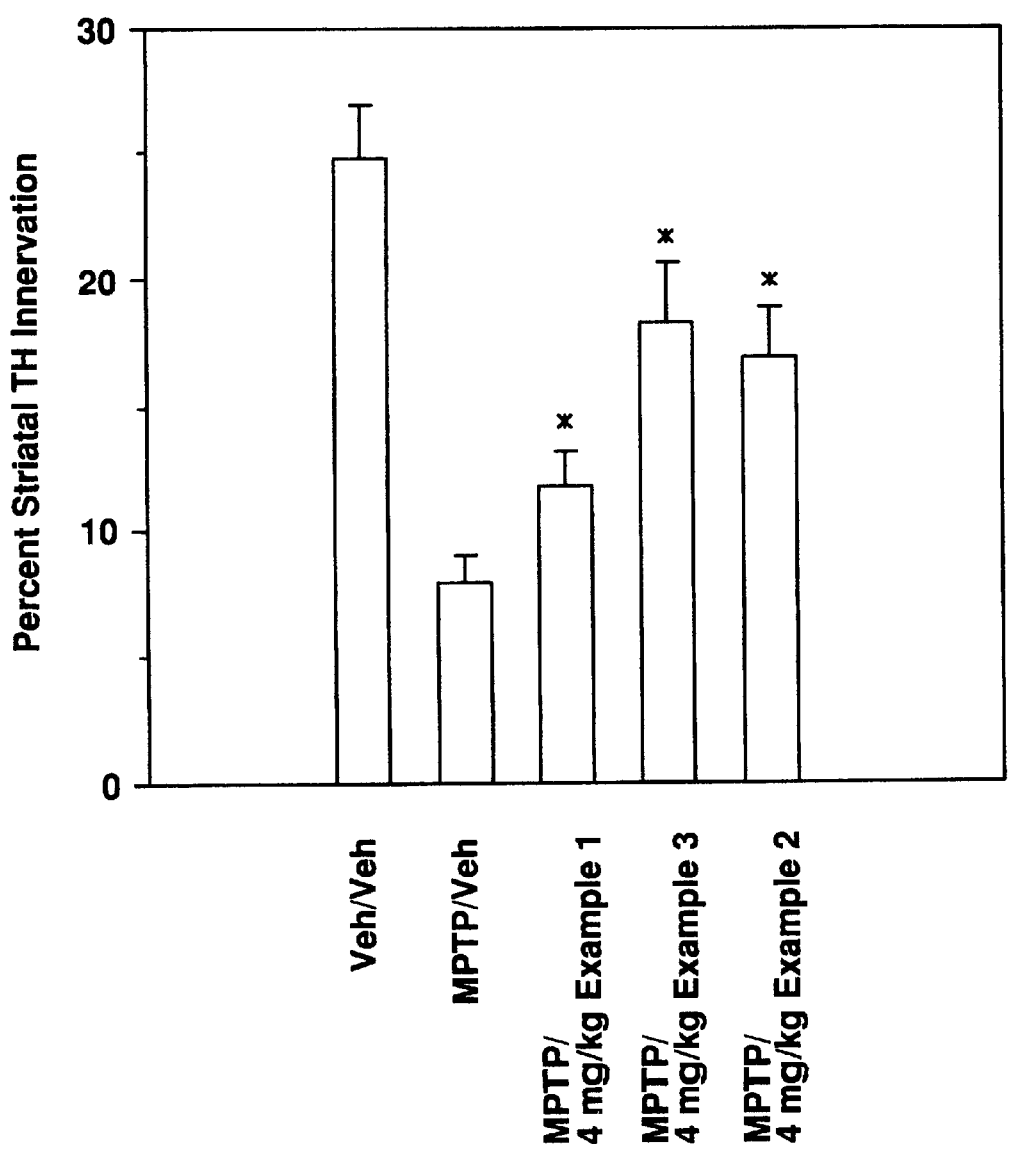
FIG. 4 presents quantitation for the recovery of TH-positive dopaminergic neurons in the striatum of animals receiving compound 1 and related compounds.

The results of these experiments are presented in TABLE IV under the column "% TH recovery". Quantitation for the recovery of TH-positive dopaminergic neurons in the striatum of animals receiving compounds of the invention, including compound 1, and for representative control and lesioned animals not receiving the test drugs, are presented in FIG. 4.

TABLE IV

| In Vitro Test Results | | | |
|---|---|---|---|
| Compound | Ki, nM | ED50, nM | % TH recovery |
| 1 | 31 | 0.4 | 23 |
| 2 | 210 | — | — |
| 3 | 85 | — | — |
| 9 | 104 | 0.5 | 61 |
| 10 | 12 | 0.8 | 54 |
| 11 | 299 | 0.36 | 53 |
| 12 | 442 | 0.025 | — |
| 14 | 313 | 0.9 | 48 |
| 28 | 362 | — | 52 |
| 29 | 1698 | — | — |
| 30 | 34 | 0.9 | 48 |
| 31 | 62 | — | — |
| 32 | 7 | — | 56 |
| 33 | 68 | — | — |
| 34 | 8.9 | 0.011 | 37.32 |
| 35 | 347 | — | — |
| 36 | 1226 | — | — |
| 37 | 366 | — | — |
| 38 | 28 | — | — |
| 39 | 259 | — | — |
| 40 | 188 | — | 25 |
| 41 | 31 | — | — |
| 42 | 757 | — | — |
| 43 | 21 | — | 50 |
| 44 | 127 | — | 28 |
| 45 | 1334 | — | — |
| 46 | 55 | — | 62 |
| 47 | 33 | — | — |
| 48 | 6 | — | — |
| 49 | 261 | — | — |
| 50 | 37 | — | — |
| 51 | 30 | — | — |
| 52 | 880 | — | — |
| 53 | 57 | — | — |
| 54 | 79 | — | — |
| 55 | 962 | — | — |
| 56 | 90 | — | — |
| 57 | 139 | — | — |
| 58 | 196 | — | — |
| 59 | 82 | — | — |
| 60 | 163 | — | — |
| 61 | 68 | — | — |
| 62 | 306 | 5 | 38 |
| 63 | 177 | — | — |

TABLE IV-continued

| In Vitro Test Results | | | |
|---|---|---|---|
| Compound | Ki, nM | ED50, nM | % TH recovery |
| 64 | 284 | — | — |
| 65 | 49 | — | 23 |
| 66 | 457 | — | 25 |
| 67 | 788 | — | — |

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

We claim:

1. A compound of formula II:

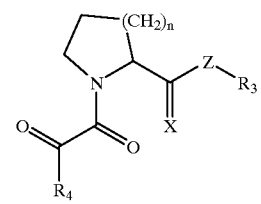

or a pharmaceutically acceptable salt, ester, or solvate thereof, wherein:

n is 1 or 2;

X is O or S;

Z is selected from the group consisting of $CH_2$, $CHR_1$ and $CR_1R_2$;

$R_1$, $R_2$, and $R_3$ are independently selected from the group consisting of $C_1$–$C_5$ straight or branched chain alkyl, $C_2$–$C_5$ straight or branched chain alkenyl, and Ar, wherein said $R_1$, $R_2$, or $R_3$ is unsubstituted or substituted with one or more substituents independently selected from the group consisting of halo, trifluoromethyl, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, and Ar;

$R_4$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, and Ar; provided that when Z is $CH_2$, $R_3$ is ethyl, X is O and n is 2, then $R_4$ is not 1,1 dimethyl propyl and;

Ar is an aromatic carbocyclic or heterocyclic group having a single ring or multiple condensed rings in which at least one ring is aromatic and may contain 1–6 heteroatom(s) selected from the group consisting of O, N, and S, wherein said Ar is unsubstituted or substituted with halo, trifluoromethyl, hydroxy, nitro, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, or amino.

2. The compound of claim 1, wherein:

n is 1; and

X is O.

3. The compound of claim 2, wherein Z is $CH_2$.

4. The compound of claim 3, wherein $R_3$ is 3-pyridylpropyl and $R_4$ is 1,1-dimethylpropyl.

5. The compound of claim 3, wherein $R_3$ is 2-phenylethyl, and $R_4$ is tert-butyl.

6. The compound of claim 3, wherein $R_3$ is 3-(4-hydroxyphenyl)propyl and $R_4$ is 1,1-dimethylpropyl.

7. The compound of claim 3, which is selected from the group consisting of:
   (2S)-3,3-dimethyl-1-[2-(5-phenylpentanoyl)pyrrolidinyl] pentane-1,2-dione;
   (2S)-3,3-dimethyl-1-[2-(5-(3-pyridyl)pyrrolidinyl] pentane-1,2-dione;
   (2S)-2-({1-oxo-5-phenyl}pentyl-1-(3,3-dimethyl-1,2-dioxobutyl)pyrrolidine;
   (2S)-3,3-dimethyl-1-[2-(5-(4-hydroxyphenyl)pentanoyl) pyrrolidinyl]pentane-1,2-dione;
   (2S)-2-({1-Oxo-5-phenyl}pentyl-1-(2-Cyclohexyl-1,2-dioxoethyl)pyrrolidine;
   2-(1-Oxo-4-phenyl)-butyl-1-(3,3-dimethyl-1,2-dioxobutyl)pyrrolidine;
   (2S)-2-[5,5-di(4-Fluorophenyl)pentanoyl]-1-(3,3 dimethyl-1,2-pentanedione)pyrrolidine; and pharmaceutically acceptable salts, esters, or solvates thereof.

8. The compound of claim 7 which is (2S)-3,3-dimethyl-1-[2-(5-(3-pyridyl)pyrrolidinyl]pentane-1,2-dione, or a pharmaceutically acceptable salt, ester, or solvate thereof.

9. The compound of claim 7 which is 2-(1-Oxo-4-phenyl)-butyl-1-(3,3-dimethyl-1-1,2-dioxobutyl) pyrrolidine, or a pharmaceutically acceptable salt, ester, or solvate thereof.

10. The compound of claim 7 which is (2S)-3,3-dimethyl-1-[2-(5-(4-hydroxyphenyl)pentanoyl)pyrrolidinyl]pentane-1,2-dione, or a pharmaceutically acceptable salt, ester, or solvate thereof.

11. The compound of claim 1, wherein:
   n is 1; and
   X is S.

12. The compound of claim 11, wherein Z is $CH_2$.

13. The compound of claim 1, wherein:
   n is 2; and
   X is O.

14. The compound of claim 13, wherein Z is $CH_2$.

15. The compound of claim 14, wherein $R_3$ is 4-phenylbutyl and $R_4$ is 1,1-dimethylpropyl.

16. The compound of claim 14, which is selected from the group consisting of:
   2-({1-Oxo-6-phenyl}-hexyl-1-(2-Cyclohexyl-1,2-dioxoethyl)piperidine;
   2-({1-oxo-6-phenyl}-hexyl)(2S)-1-(3,3-dimethyl-1,2-dioxopentyl)piperidine;
   3,3-Dimethyl-1-[2-(5-phenylpentanoyl)piperidino]-1,2-pentanedione; and
pharmaceutically acceptable salts, esters, or solvates thereof.

17. The compound of claim 16 which is 2-({1-oxo-6-phenyl}-hexyl)(2S)-1-(3,3-dimethyl-1,2-dioxopentyl) piperidine or a pharmaceutically acceptable salt, ester, or solvate thereof.

18. The compound of claim 1, wherein:
   n is 2; and
   X is S.

19. The compound of claim 18, wherein Z is $CH_2$.

20. The compound of claim 18, wherein Z is $CHR_1$.

21. The compound of claim 13, which is 2-({1-Oxo-[2-{2'-phenyl}ethyl]-4-phenyl}-butyl-1-(3,3-dimethyl-1,2-dioxobutyl)piperidine.

22. A pharmaceutical composition comprising:
   (i) an effective amount of the compound of claim 1; and
   (ii) a pharmaceutically acceptable carrier.

23. The pharmaceutical composition of claim 22, wherein, in said compound:
   n is 1; and
   X is O.

24. The pharmaceutical composition of claim 23, wherein, in said compound, Z is $CH_2$.

25. The pharmaceutical composition of claim 24, wherein $R_3$ is 3-pyridylpropyl and $R_4$ is 1,1-dimethylpropyl.

26. The pharmaceutical composition of claim 24, wherein $R_3$ is 2-phenylethyl, and $R_4$ is tert-butyl.

27. The pharmaceutical composition of claim 24, wherein $R_3$ is 3-(4-hydroxyphenyl)propyl and $R_4$ is 1,1-dimethylpropyl.

28. The pharmaceutical composition of claim 24, wherein said compound is selected from the group consisting of:
   (2S)-3,3-dimethyl-1-[2-(5-phenylpentanoyl)pyrrolidinyl] pentane-1,2-dione;
   (2S)-3,3-dimethyl-1-[2-(5-(3-pyridyl)pyrrolidinyl] pentane-1,2-dione;
   (2S)-2-({1-oxo-5-phenyl}pentyl-1-(3,3-dimethyl-1,2-dioxobutyl)pyrrolidine;
   (2S)-3,3-dimethyl-1-[2-(5-(4-hydroxyphenyl)pentanoyl) pyrrolidinyl]pentane-1,2-dione;
   (2S)-2-({1-Oxo-5-phenyl}pentyl-1-(2-Cyclohexyl-1,2-dioxoethyl)pyrrolidine;
   2-(1-Oxo-4-phenyl)-butyl-1-(3,3-dimethyl-1,2-dioxobutyl)pyrrolidine;
   (2S)-2-[5,5-di(4-Fluorophenyl)pentanoyl]-1-(3,3 dimethyl-1,2-pentanedione)pyrrolidine; and
pharmaceutically acceptable salts, esters, or solvates thereof.

29. The pharmaceutical composition of claim 28 wherein said compound is (2S)-3,3-dimethyl-1-[2-(5-(3-pyridyl) pyrrolidinyl]pentane-1,2-dione, or a pharmaceutically acceptable salt, ester, or solvate thereof.

30. The pharmaceutical composition of claim 28 wherein said compound is 2-(1-Oxo-4-phenyl)-butyl-1-(3,3-dimethyl-1,2-dioxobutyl)pyrrolidine, or a pharmaceutically acceptable salt, ester, or solvate thereof.

31. The pharmaceutical composition of claim 28 wherein said compound is (2S)-3,3-dimethyl-1-[2-(5-(4-hydroxyphenyl)pentanoyl)pyrrolidinyl]pentane-1,2-dione, or a pharmaceutically acceptable salt, ester, or solvate thereof.

32. The pharmaceutical composition of claim 22, wherein, in said compound:
   n is 1; and
   X is S.

33. The pharmaceutical composition of claim 32, wherein, in said compound, Z is $CH_2$.

34. The pharmaceutical composition of claim 22, wherein, in said compound:
   n is 2; and
   X is O.

35. The pharmaceutical composition of claim 34, wherein, in said compound, Z is $CH_2$.

36. The pharmaceutical composition of claim 35, wherein $R_3$ is 4-phenylbutyl and $R_4$ is 1,1-dimethylpropyl.

37. The pharmaceutical composition of claim 35, wherein said compound is selected from the group consisting of:
   2-({1-Oxo-6-phenyl}-hexyl-1-(2-Cyclohexyl-1,2-dioxoethyl)piperidine;

2-({1-oxo-6-phenyl}-hexyl)(2S)-1-(3,3-dimethyl-1,2-dioxopentyl)piperidine;

3,3-Dimethyl-1-[2-(5-phenylpentanoyl)piperidino]-1,2-pentanedione; and pharmaceutically acceptable salts, esters, or solvates thereof.

38. The pharmaceutical composition of claim 37 wherein said compound is 2-({1-oxo-6-phenyl}-hexyl)(2S)-1-(3,3-dimethyl-1,2-dioxopentyl)piperidine.

39. The pharmaceutical composition of claim 22, wherein, in said compound:

n is 2; and

X is S.

40. The pharmaceutical composition of claim 39, wherein, in said compound, Z is $CH_2$.

41. The pharmaceutical composition of claim 39, wherein, in said compound, Z is $CHR_1$.

42. The pharmaceutical composition of claim 34, wherein said compound is 2-({1-Oxo-[2-{2'-phenyl}ethyl]-4-phenyl}-butyl-1-(3,3-dimethyl-1,2-dioxobutyl)piperidine.

43. A method for effecting a neuronal activity in an animal, comprising administering to the animal an effective amount of the compound of claim 1.

44. The method of claim 43, wherein the neuronal activity is selected from the group consisting of stimulation of damaged neurons, promotion of neuronal regeneration, prevention of neurodegeneration and treatment of neurological disorder.

45. The method of claim 44, wherein the neurological disorder is selected from the group consisting of peripheral neuropathy caused by physical injury or disease state, traumatic injury to the brain, physical damage to the spinal cord, stroke associated with brain damage, and neurological disorder relating to neurodegeneration.

46. The method of claim 45, wherein the neurological disorder relating to neurodegeneration is selected from the group consisting of Alzheimer's Disease, Huntington's Disease, Parkinson's Disease, and amyotrophic lateral sclerosis.

47. The method of claim 43, wherein, in said compound:

n is 1; and

X is O.

48. The method of claim 47, wherein, in said compound, Z is $CH_2$.

49. The method of claim 48, wherein $R_3$ is 3-pyridylpropyl and $R_4$ is 1,1-dimethylpropyl.

50. The method of claim 48, wherein $R_3$ is 2-phenylethyl, and $R_4$ is tert-butyl.

51. The method of claim 48, wherein $R_3$ is 3-(4-hydroxyphenyl)propyl and $R_4$ is 1,1-dimethylpropyl.

52. The method of claim 48, wherein said compound is selected from the group consisting of:

(2S)-3,3-dimethyl-1-[2-(5-phenylpentanoyl)pyrrolidinyl]pentane-1,2-dione;

(2S)-3,3-dimethyl-1-[2-(5-(3-pyridyl)pyrrolidinyl]pentane-1,2-dione;

(2S)-2-({1-oxo-5-phenyl}pentyl-1-(3,3-dimethyl-1,2-dioxobutyl)pyrrolidine;

(2S)-3,3-dimethyl-1-[2-(5-(4-hydroxyphenyl)pentanoyl)pyrrolidinyl]pentane-1,2-dione;

(2S)-2-({1-Oxo-5-phenyl}pentyl-1-(2-Cyclohexyl-1,2-dioxoethyl)pyrrolidine;

2-(1-Oxo-4-phenyl)-butyl-1-(3,3-dimethyl-1,2-dioxobutyl)pyrrolidine;

(2S)-2-[5,5-di(4-Fluorophenyl)pentanoyl]-1(3,3-dimethyl-1,2-pentanedione)pyrrolidine; and pharmaceutically acceptable salts, esters, or solvates thereof.

53. The method of claim 52 wherein said compound is (2S)-3,3-dimethyl-1-[2-(5-(3-pyridyl)pyrrolidinyl]pentane-1,2-dione, or a pharmaceutically acceptable salt, ester, or solvate thereof.

54. The method of claim 52 wherein said compound is 2-(1-Oxo-4-phenyl)butyl-1-(3,3-dimethyl-1,2-dioxobutyl)pyrrolidine, or a pharmaceutically acceptable salt, ester, or solvate thereof.

55. The method of claim 52 wherein said compound 2S-3,3-dimethyl-1-[2-(5-(4-hydroxyphenyl)pentanoyl)pyrrolidinyl]pentane-1,2-dione, or a pharmaceutically acceptable salt, ester, or solvate thereof.

56. The method of claim 43, wherein, in said compound:

n is 1; and

X is S.

57. The method of claim 56, wherein, in said compound, Z is $CH_2$.

58. The method of claim 43, wherein, in said compound:

n is 2; and

X is O.

59. The method of claim 58, wherein, in said compound, Z is $CH_2$.

60. The method of claim 59, wherein $R_3$ is 4-phenylbutyl and $R_4$ is 1,1-dimethylpropyl.

61. The method of claim 59, wherein said compound is selected from the group consisting of:

2-({1-Oxo-6-phenyl}-hexyl-1-(2-Cyclohexyl-1,2-dioxoethyl)piperidine;

2-({1-oxo-6-phenyl}-hexyl)(2S)-1-(3,3-dimethyl-1,2-dioxopentyl)piperidine;

3,3-Dimethyl-1-[2-(5-phenylpentanoyl)piperidino]-1,2-pentanedione; and pharmaceutically acceptable salts, esters, or solvates thereof.

62. The method of claim 61, wherein said compound is 2-({1-oxo-6-phenyl}-hexyl)(2S)-1-(3,3-dimethyl-1,2-dioxopentyl)piperidine.

63. The method of claim 43, wherein, in said compound:

n is 2; and

X is S.

64. The method of claim 63, wherein, in said compound, Z is $CH_2$.

65. The method of claim 63, wherein in said compound, Z is $CHR_1$.

66. The method of claim 58, wherein said compound is 2-({1-Oxo-[2-{2'-phenyl}ethyl]-4-phenyl}-butyl-1-(3,3-dimethyl-1,2-dioxobutyl)piperidine.

67. The compound of claim 1 wherein Ar is selected from the group comprising phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, pyrrolinyl, quinolinyl, isoquinolinyl, tetrahydroquinolinyl, quinolizinyl, furyl, thiophenyl, imidazolyl, oxazolyl, benzoxazolyl, thiazolyl, isothiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, dioxolyl, imidazolinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

68. The compound of claim 3, which is selected from the group consisting of:

(2S)-2-({1-oxo-4-phenyl}butyl-1-(3,3-dimethyl-1,2-dioxopentyl)pyrrolidine;

(2S)-2-({1-oxo-6-(3-pyridyl)hexyl-1-(3,3-dimethyl-1,2-dioxopentyl)pyrrolidine; and 3,3 dimethyl-1-[(2S)-2-(5-(3-pyridyl)pentanoyl)-1-pyrrolidine]-1,2-pentanedione.

69. A compound comprising (2S)-2-({1-oxo-4-phenyl}butyl-1-(3,3-dimethyl-1,2-dioxopentyl)pyrrolidine.

70. A compound comprising (2S)-2-({1-oxo-6-(3-pyridyl)hexyl-1-(3,3-dimethyl-1,2-dioxopentyl)pyrrolidine.

71. A compound comprising 3,3 dimethyl-1-[(2S)-2-(5-(3-pyridyl)pentanoyl)-1-pyrrolidine]-1,2-pentanedione.

72. A compound comprising (2S)-2-({1-oxo-4-phenyl}butyl-1-(3,3 dimethyl-1,2-dioxobutyl)pyrrolidine.

73. A compound comprising (2S)-3,3-dimethyl-1-[2-(5-(4-hydroxyphenyl)pentanoyl)pyrrolidinyl]pentane-1,2-dione.

74. The pharmaceutical composition of claim 24, wherein said compound is selected from the group consisting of:

(2S)-2-({1-oxo-4-phenyl}butyl-1-(3,3-dimethyl-1,2-dioxopentyl)pyrrolidine;

(2S)-2-({1-oxo-6-(3-pyridyl)hexyl-1-(3,3-dimethyl-1,2-dioxopentyl)pyrrolidine; and 3,3 dimethyl-1-[(2S)-2-(5-(3-pyridyl)pentanoyl)-1-pyrrolidine]-1,2-pentanedione.

75. The method of claim 48, wherein said compound is selected from the group consisting of:

(2S)-2-({1-oxo-4-phenyl}butyl-1-(3,3-dimethyl-1,2-dioxopentyl)pyrrolidine;

(2S)-2-({1-oxo-6-(3-pyridyl)hexyl-1-(3,3-dimethyl-1,2-dioxopentyl)pyrrolidine; and 3,3 dimethyl-1-[(2S)-2-(5-(3-pyridyl)pentanoyl)-1-pyrrolidine]-1,2-pentanedione.

* * * * *

UNITED STATES PATENT AND TRADEMARK OFFICE
CERTIFICATE OF CORRECTION

PATENT NO.    : 6,218,424 B1
DATED         : April, 17, 2001
INVENTOR(S)   : Hamilton, Li It is certified that error appears in the above-identified patent and that said Letters Patent is hereby corrected as shown below:

Column 17,
Line 61, replace "$C_{1-6}$" with -- $C_1$-$C_6$ --.

Column 26,
Line 24, replace "(t, 3H, $J=_{7.5}$);" with -- (t, 3H, J=7.5); --.

Column 27,
Lines 27-28, replace "(t, 2H, $J=_{7.7}$);" with -- (t, 2H, J=7.7); --.
Line 47, replace "(2S3)" with -- (2S) --.

Signed and Sealed this

Fourth Day of December, 2001

Attest:

NICHOLAS P. GODICI
*Attesting Officer*   *Acting Director of the United States Patent and Trademark Office*